United States Patent [19]

Saxena

[11] Patent Number: 5,212,637
[45] Date of Patent: May 18, 1993

[54] METHOD OF INVESTIGATING MAMMOGRAMS FOR MASSES AND CALCIFICATIONS, AND APPARATUS FOR PRACTICING SUCH METHOD

[75] Inventor: Kripa C. Saxena, San Jose, Calif.

[73] Assignee: Stereometrix Corporation, San Jose, Calif.

[21] Appl. No.: 441,452

[22] Filed: Nov. 22, 1989

[51] Int. Cl.[5] .................................... G06F 15/42
[52] U.S. Cl. .............................. 364/413.26; 382/6
[58] Field of Search .................. 364/413.13, 413.26; 382/6, 19, 22, 54; 378/99; 358/111, 167

[56] References Cited

U.S. PATENT DOCUMENTS

| 4,301,472 | 11/1981 | Danes | 358/163 |
| 4,739,521 | 4/1988 | Akimoto | 455/612 |
| 4,839,807 | 6/1989 | Doi et al. | 364/413.13 |
| 4,876,509 | 10/1989 | Perimutler | 324/309 |
| 5,016,173 | 5/1991 | Kenet et al. | 364/413.13 |

OTHER PUBLICATIONS

"Mammogram Inspection By Computer", Spiesberger.

Primary Examiner—Gail O. Hayes
Attorney, Agent, or Firm—Flehr, Hohbach, Test, Albritton & Herbert

[57] ABSTRACT

A method and apparatus as described facilitating the investigation of a human breast for a malignancy. The apparatus includes an optical assembly which includes a camera for acquiring information from a mammogram. This information is fed to a programmed computer which applied preselected criteria to identify suspicious masses and calcifications depicted by the mammogram. It further includes a graphics monitor for, among other things, displaying a reconstruction of the mammogram having the masses and the calcifications highlighted. The optical assembly also includes a zoom lens on the camera enabling one to obtain a magnified view on the monitor via the camera of a particular region it is desired to be investigated in more detail. The method of the invention includes optically analyzing a mammogram to acquire information defining characteristics of the breast desired to be analyzed, applying preselected criteria to such information, and thereafter displaying the results.

27 Claims, 40 Drawing Sheets

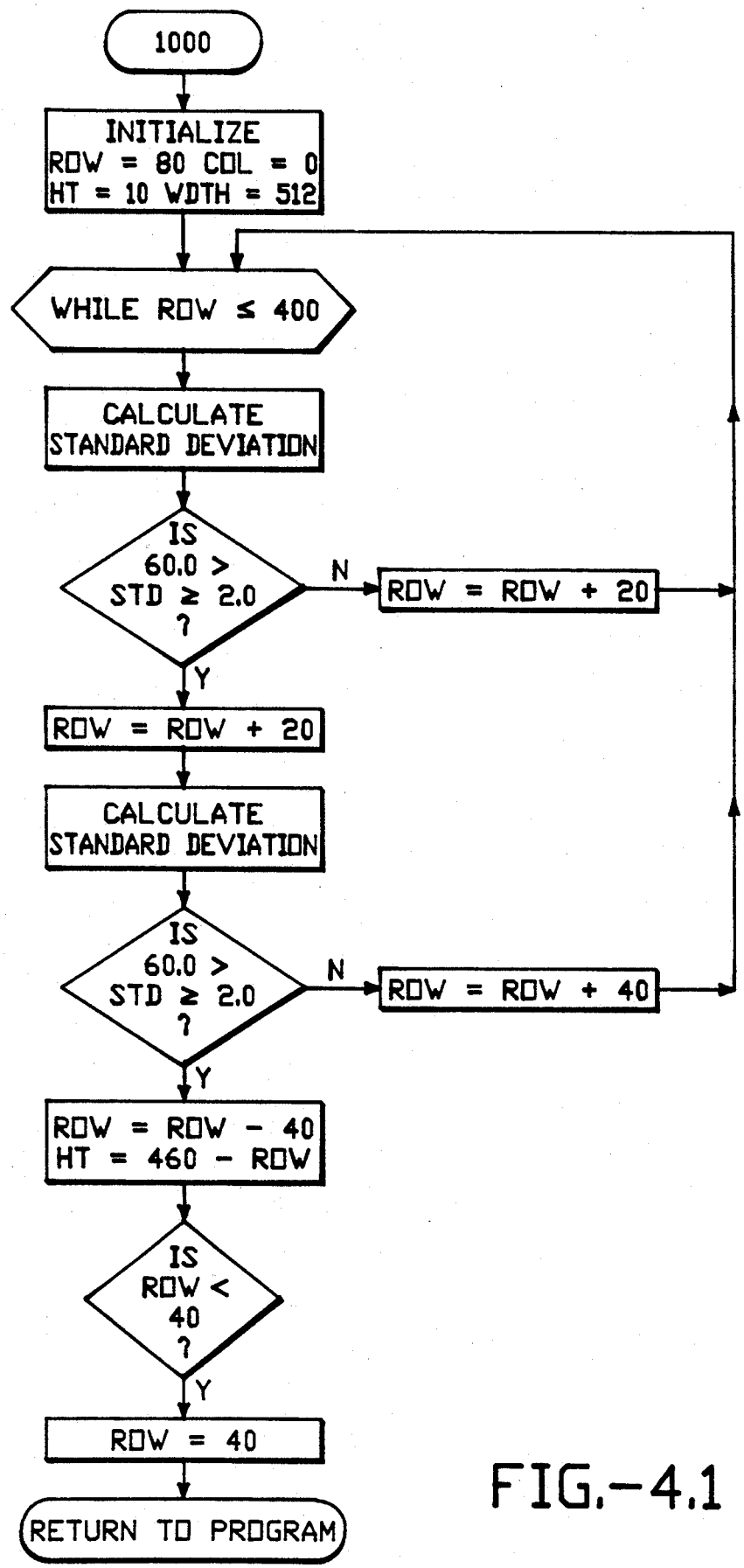
FIG.-4.1

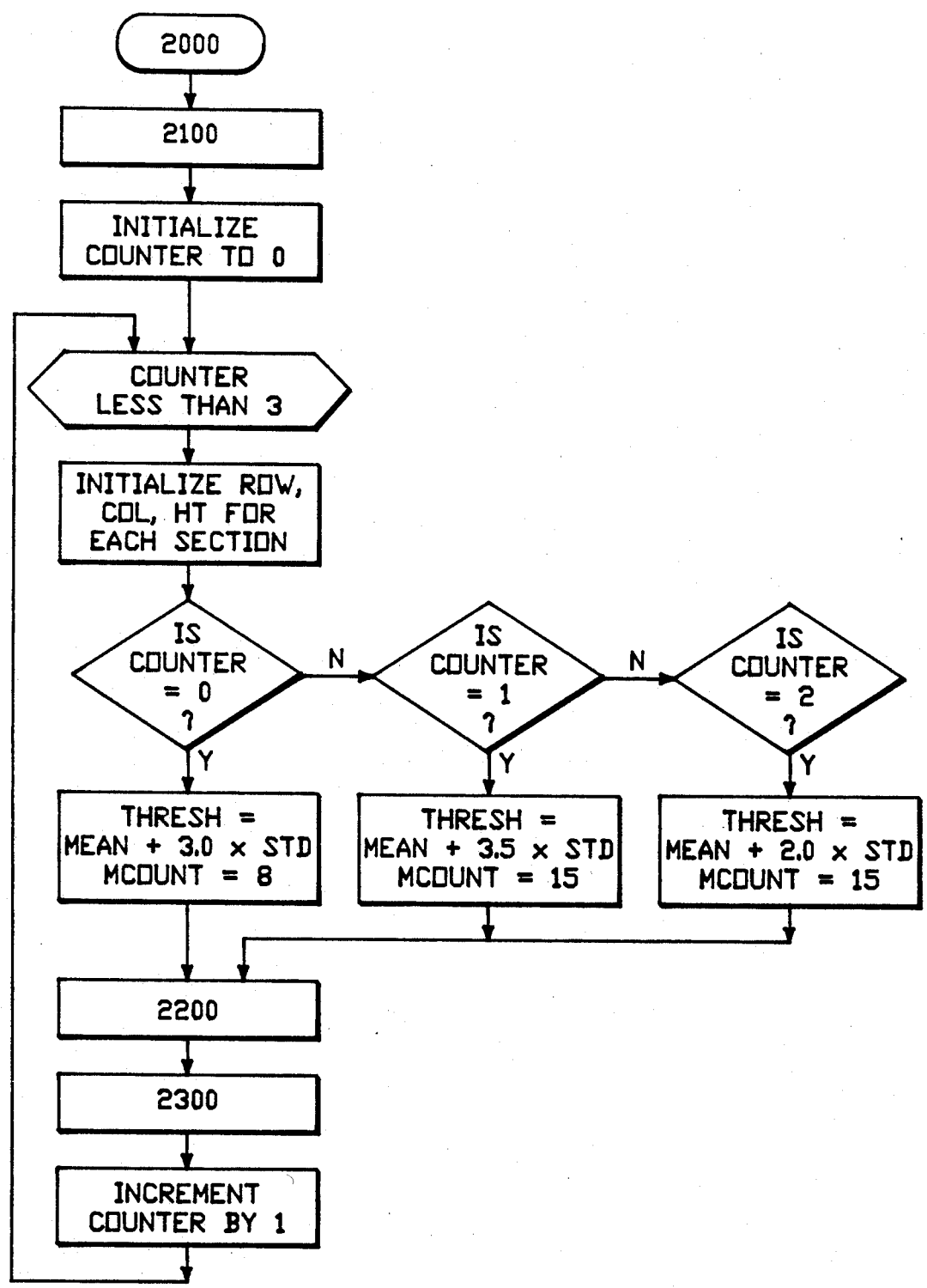
FIG.-4.2

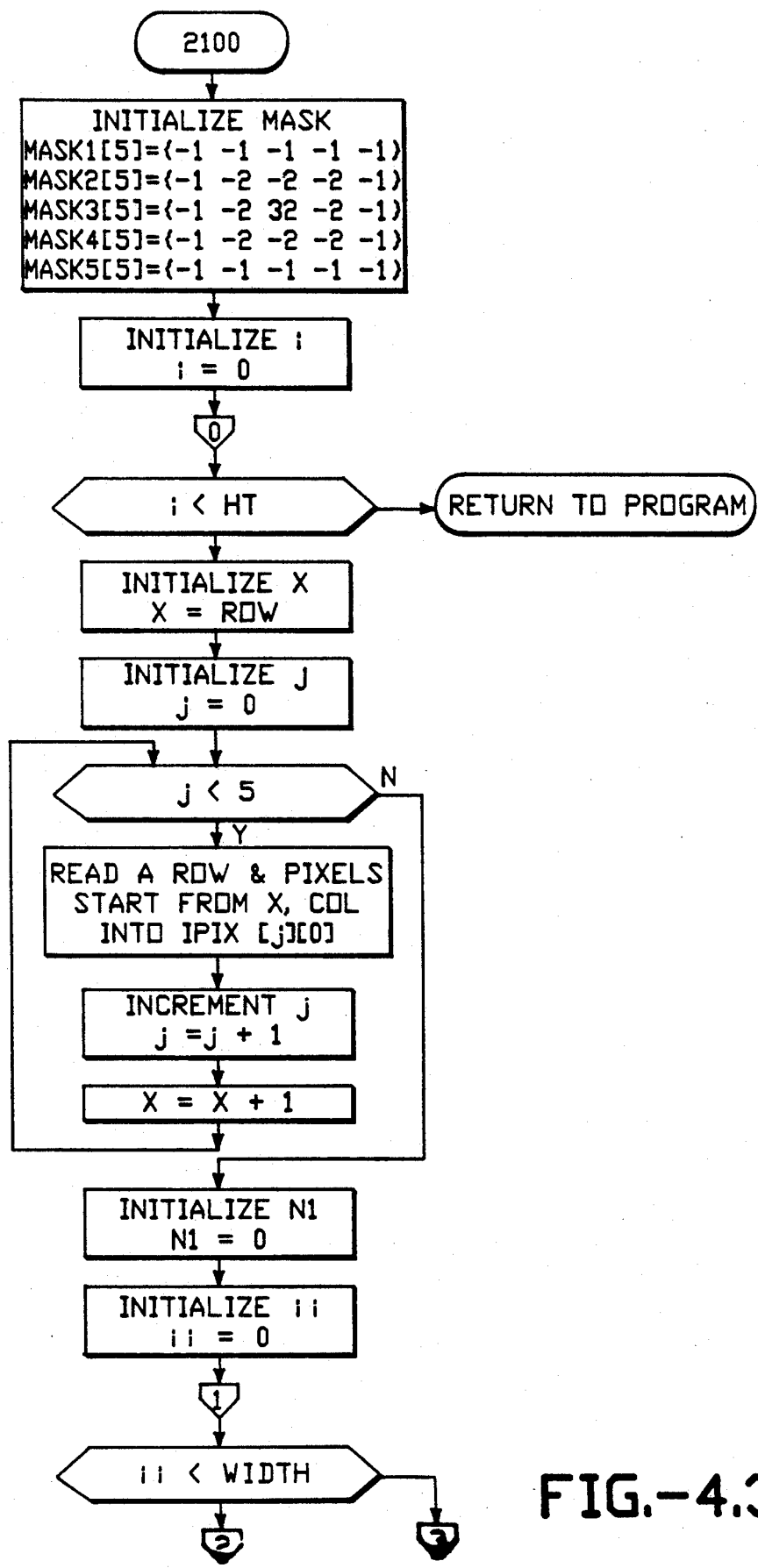
FIG.-4.3

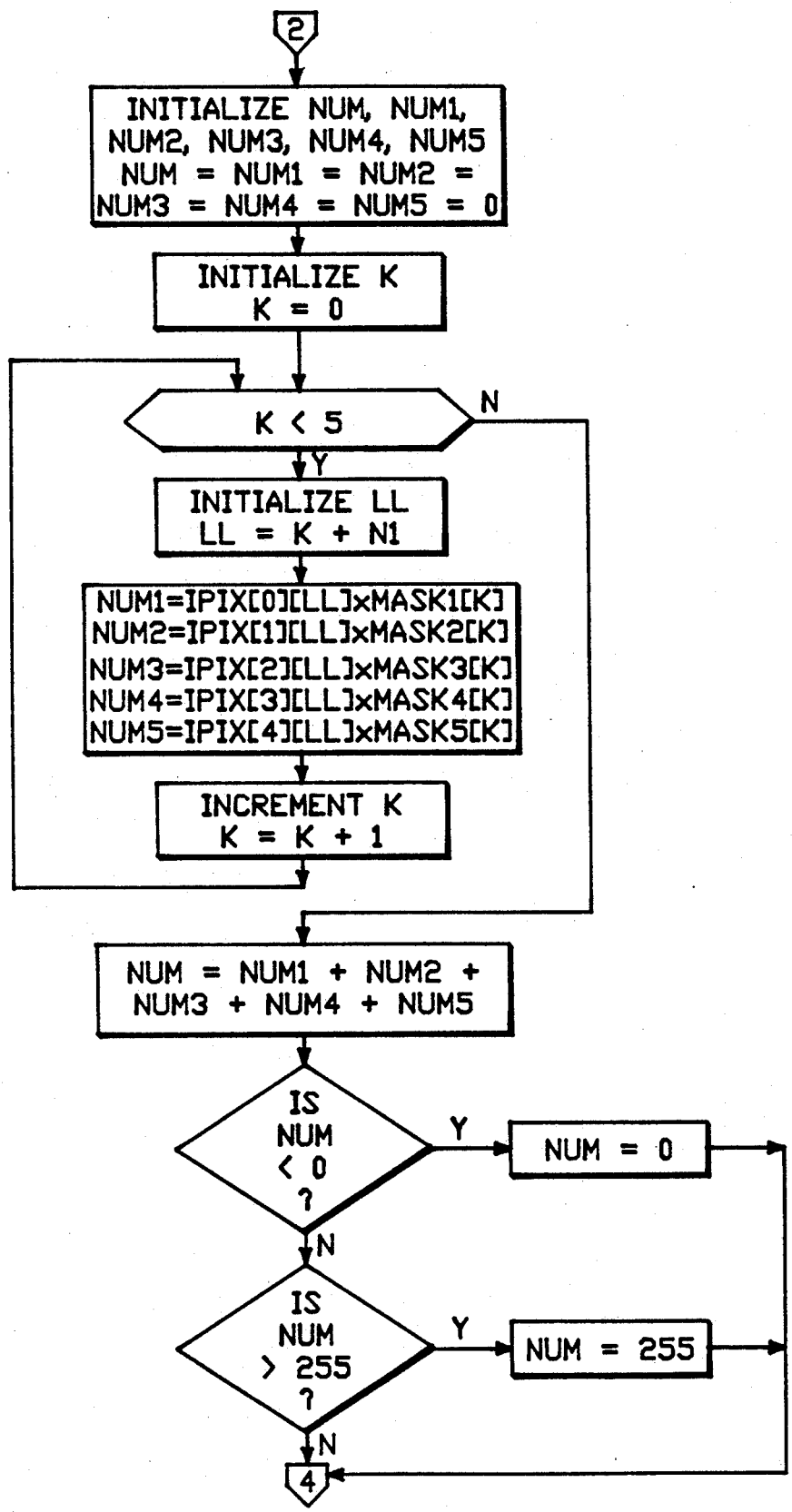
FIG.-4.4

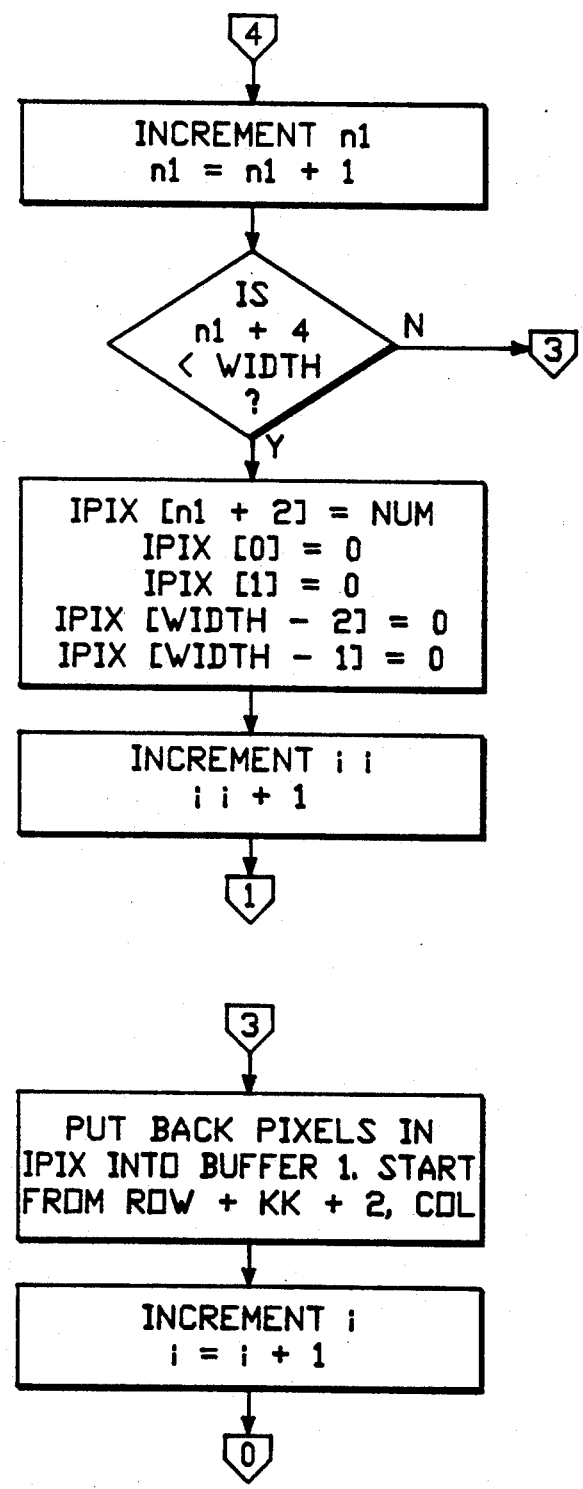
FIG.-4.5

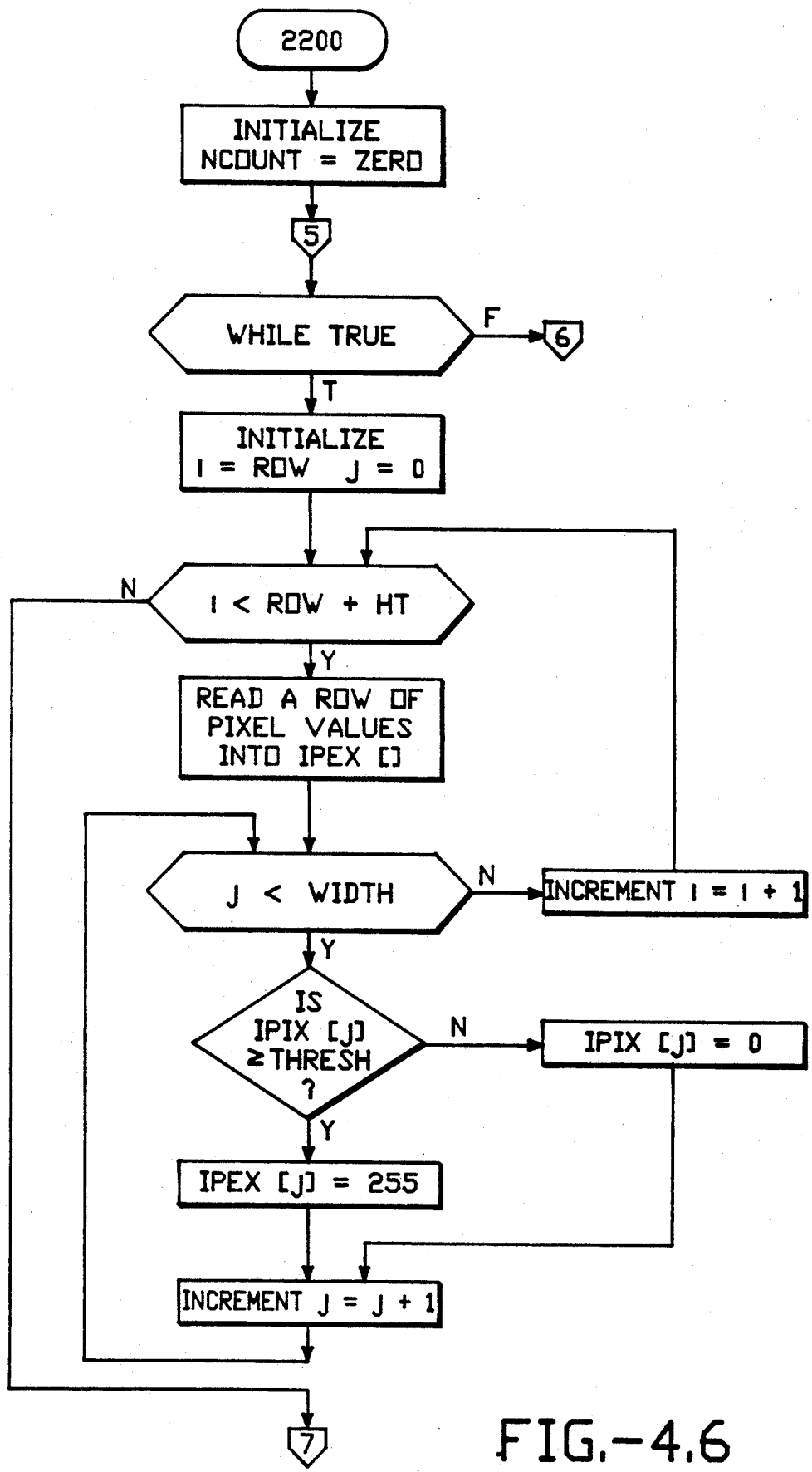
FIG.-4.6

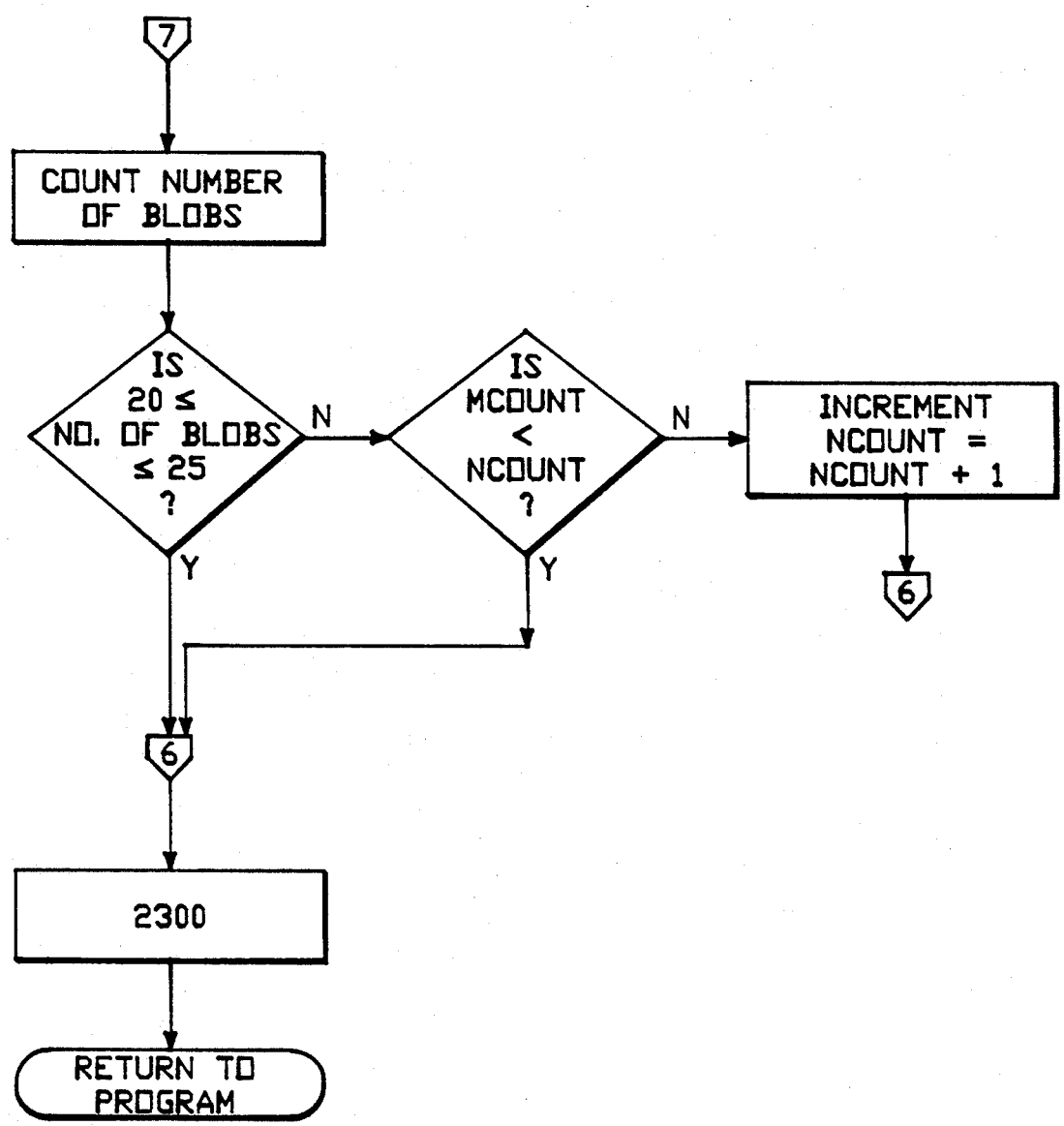
FIG.-4.7

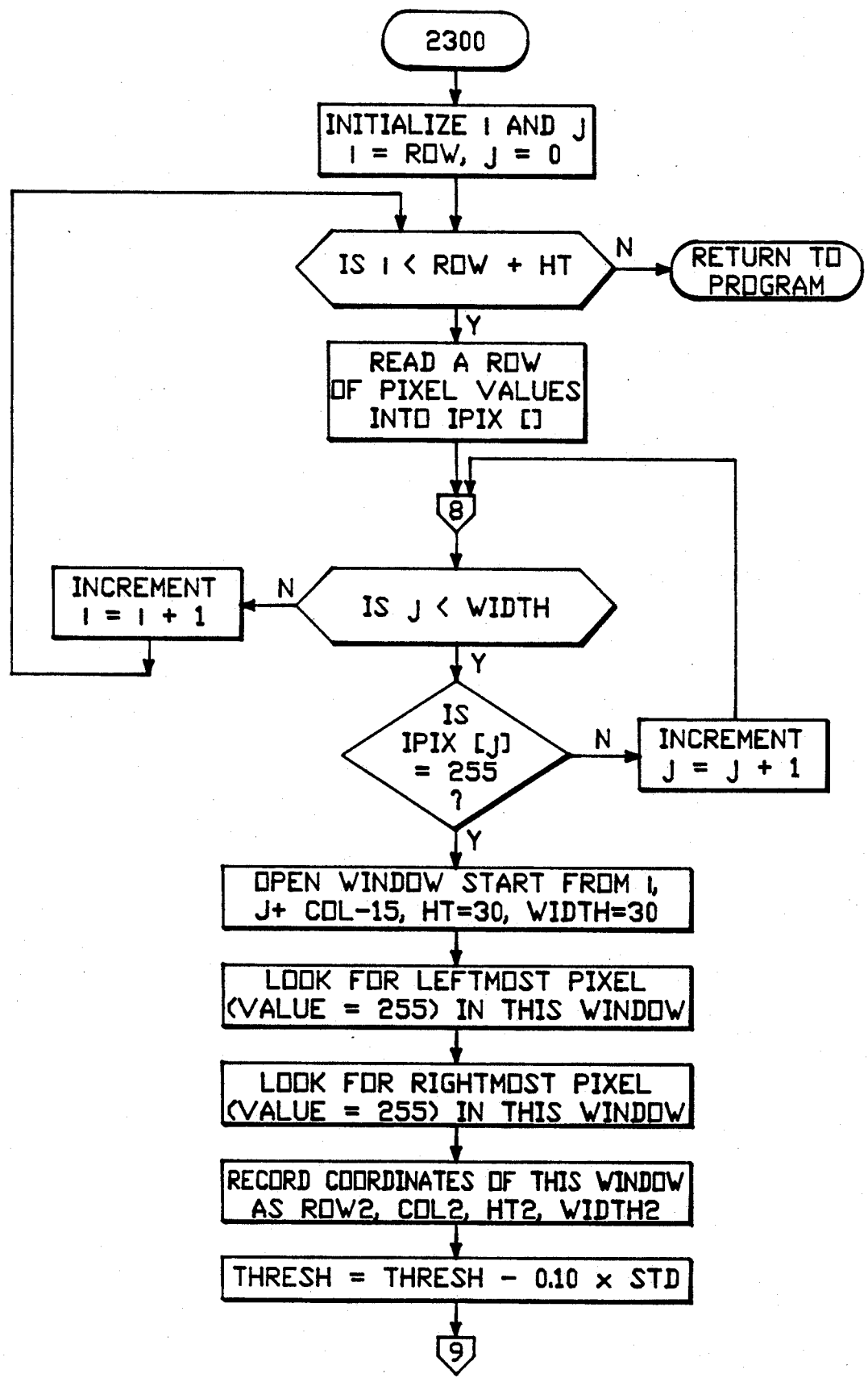
FIG.-4.8

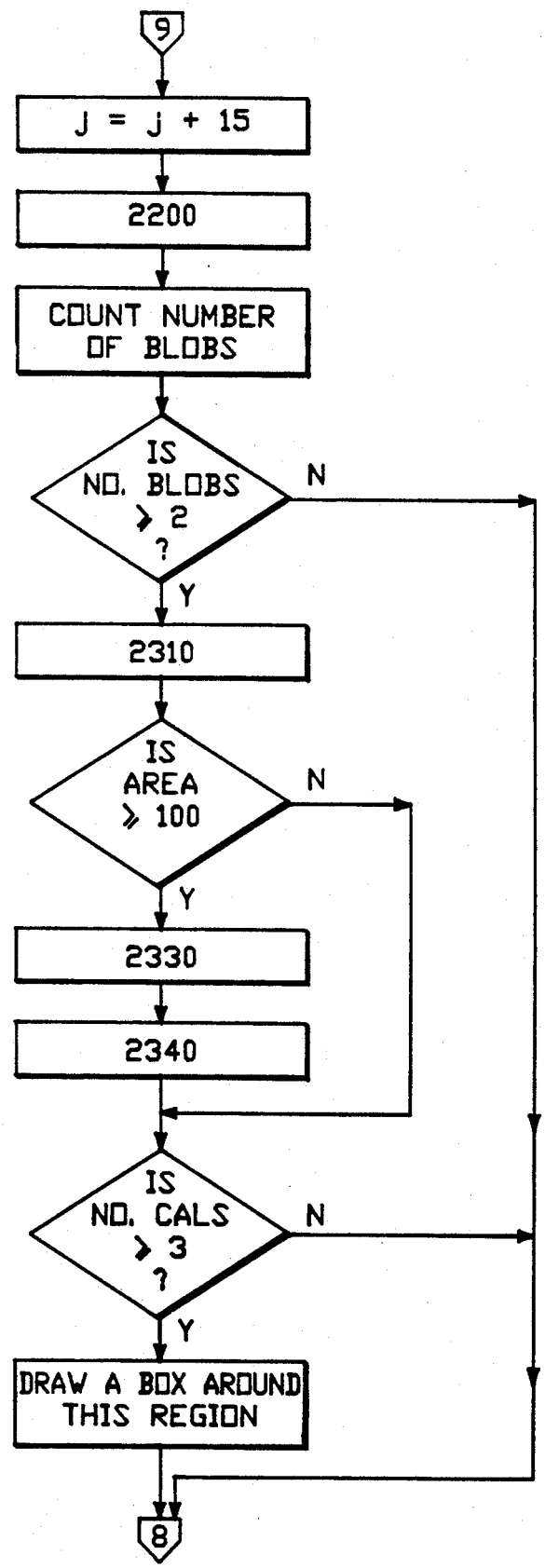
FIG.-4.9

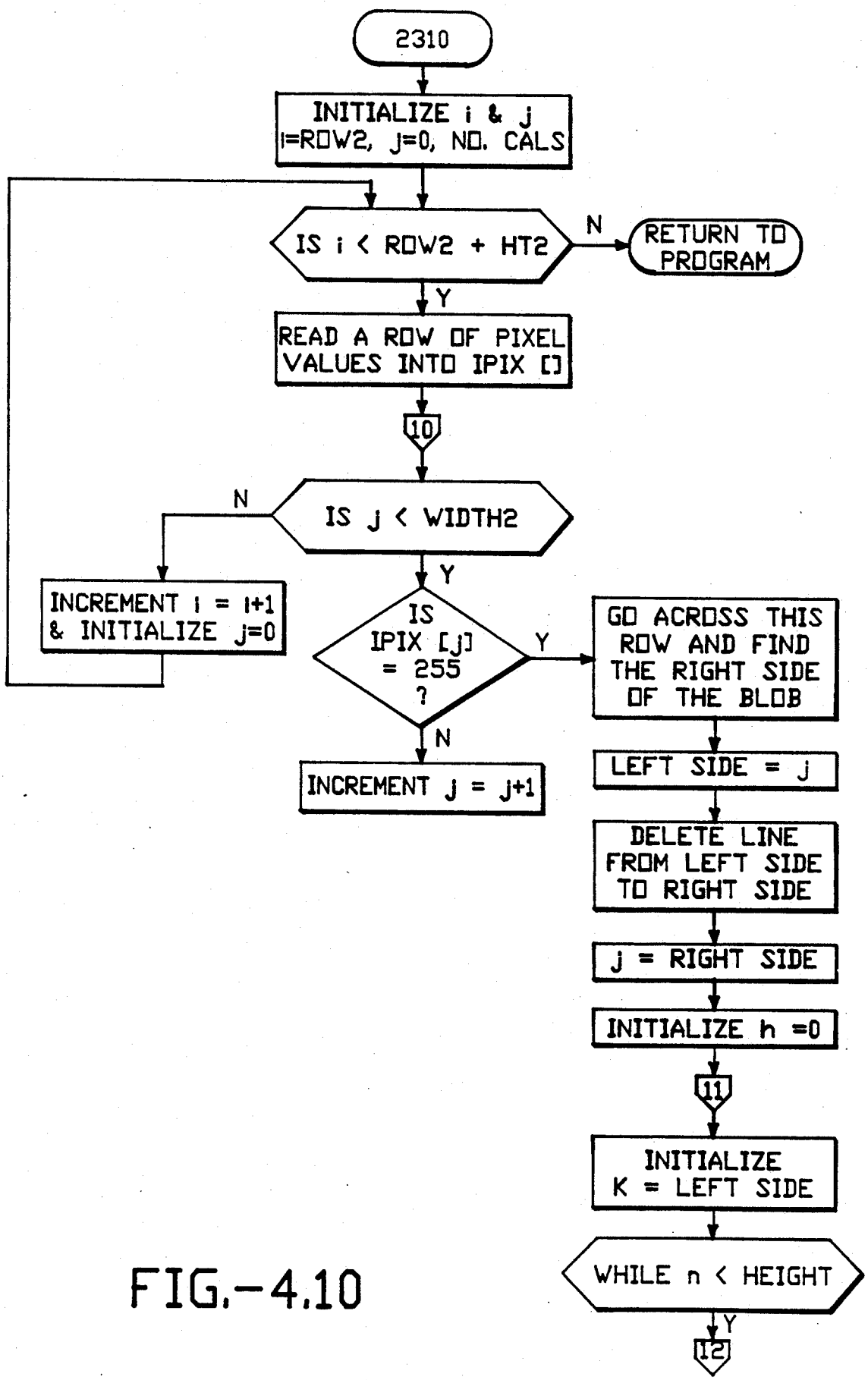
FIG.-4.10

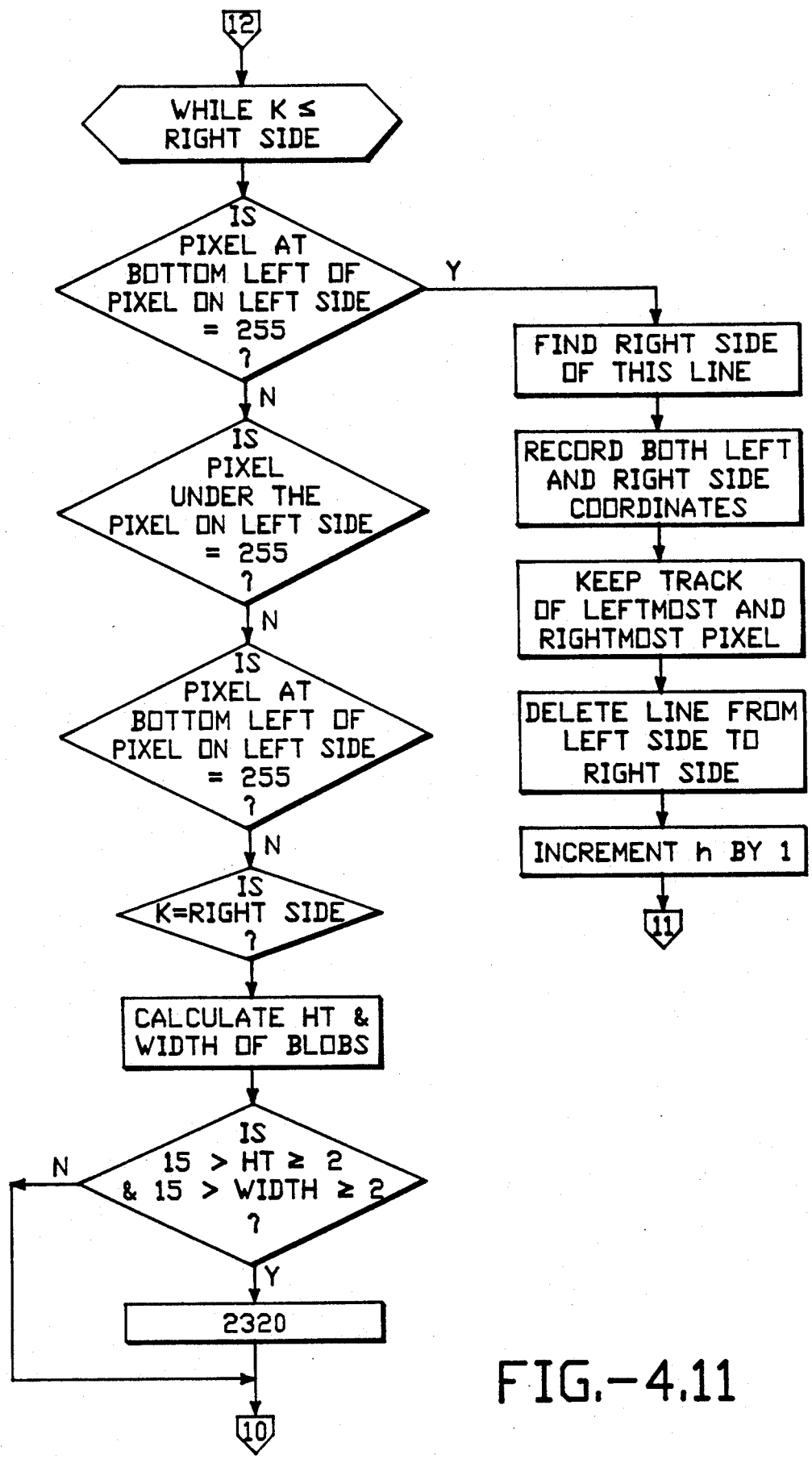
FIG.-4.11

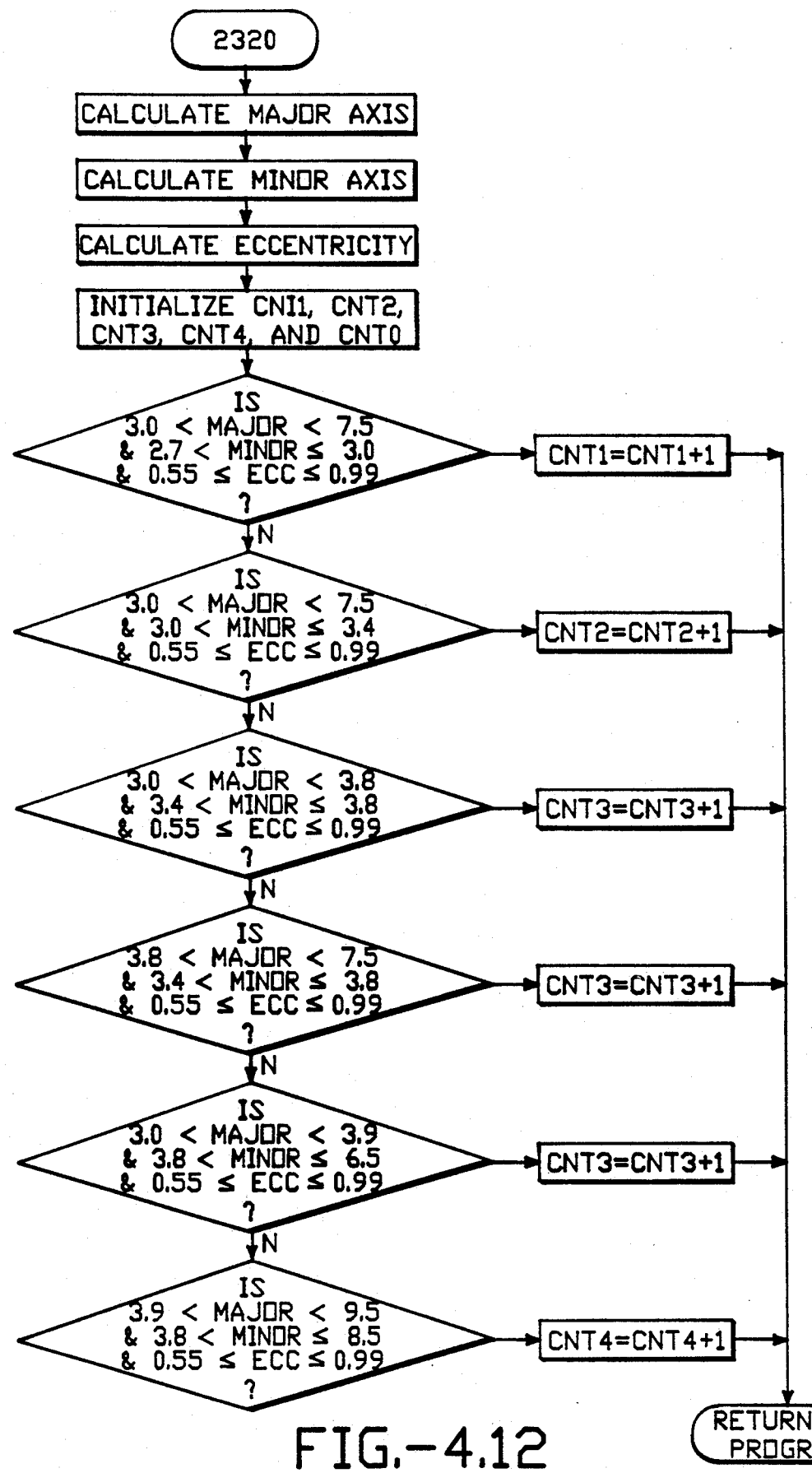
FIG.-4.12

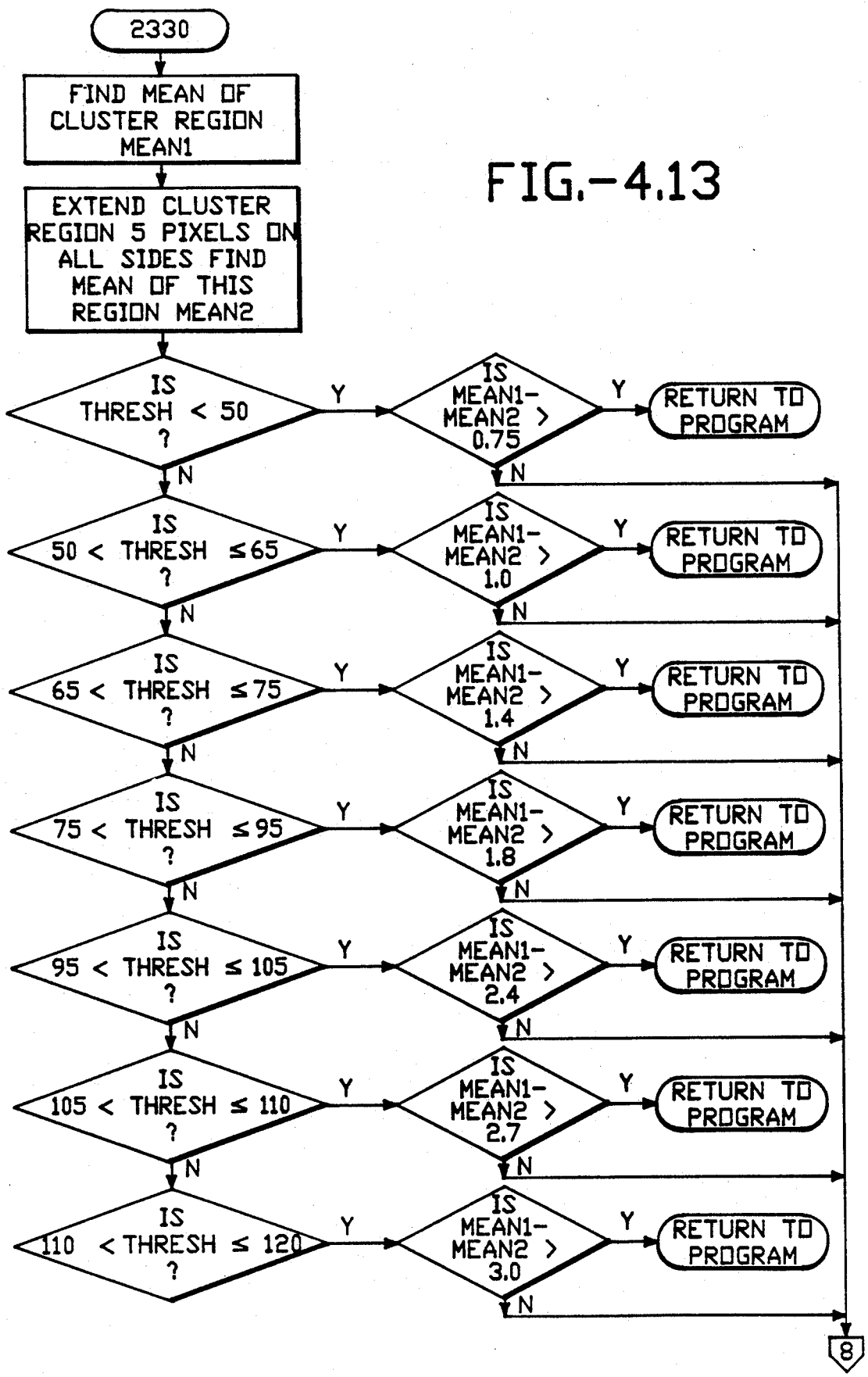
FIG.-4.13

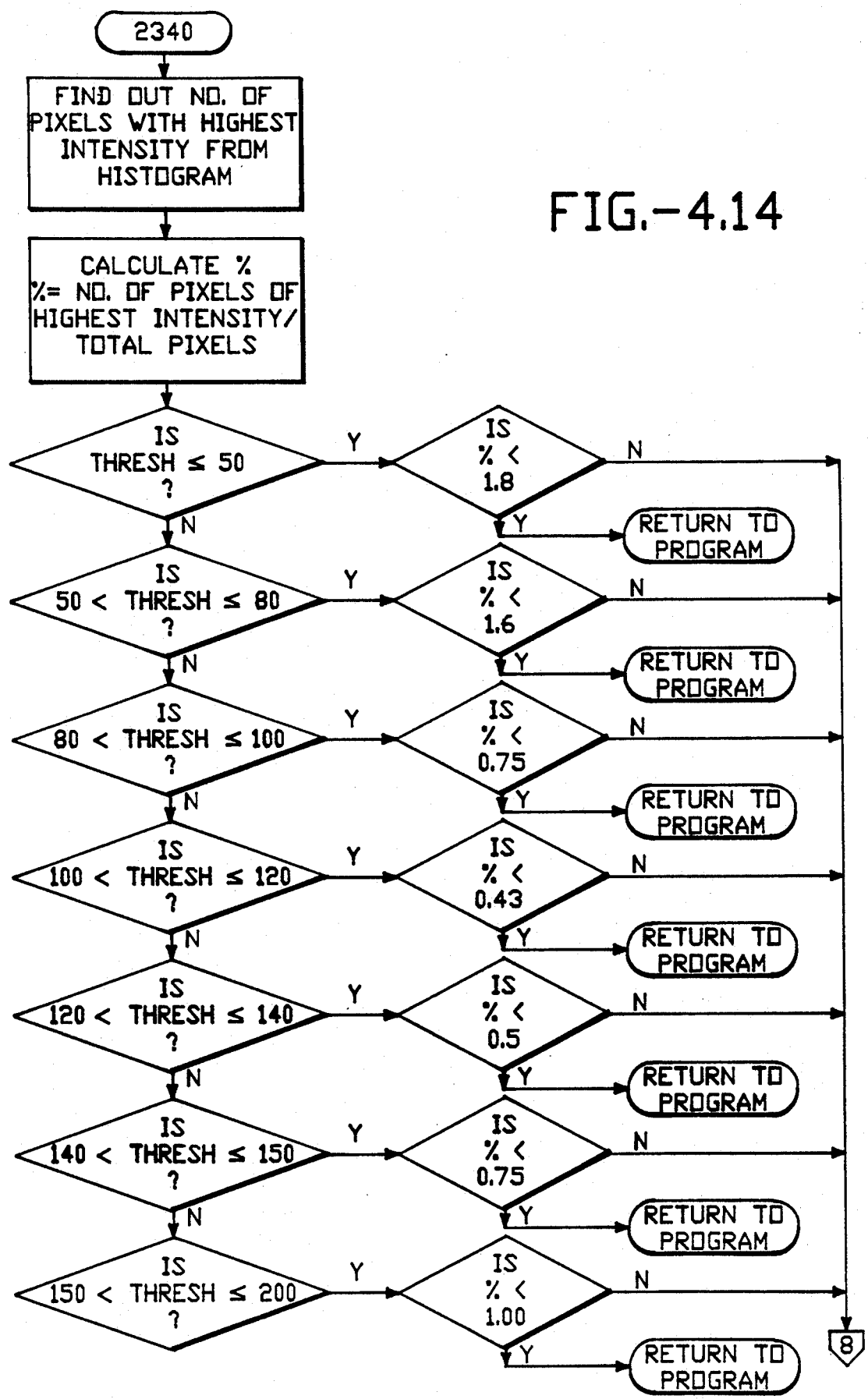
FIG.-4.14

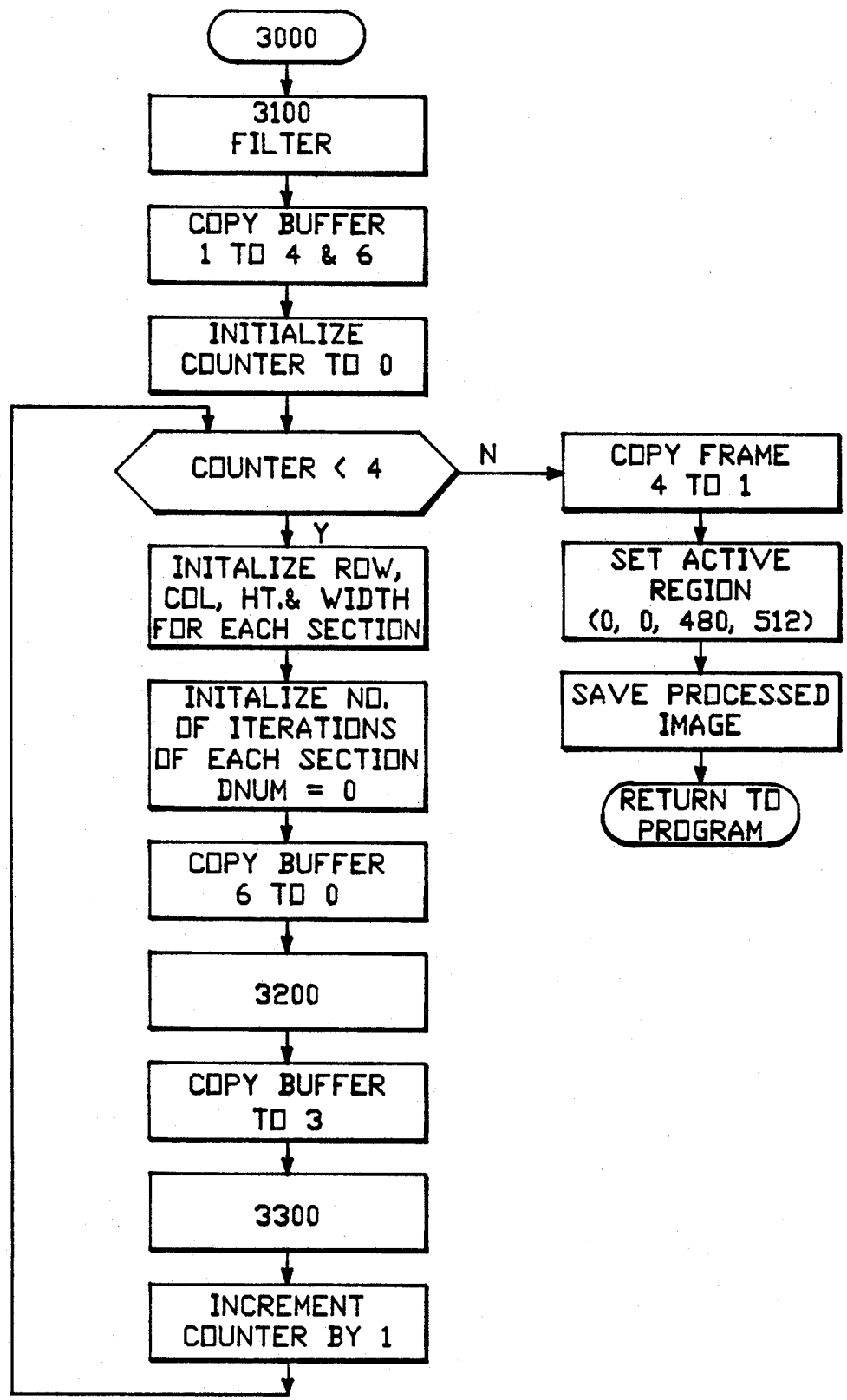
FIG.-4.15

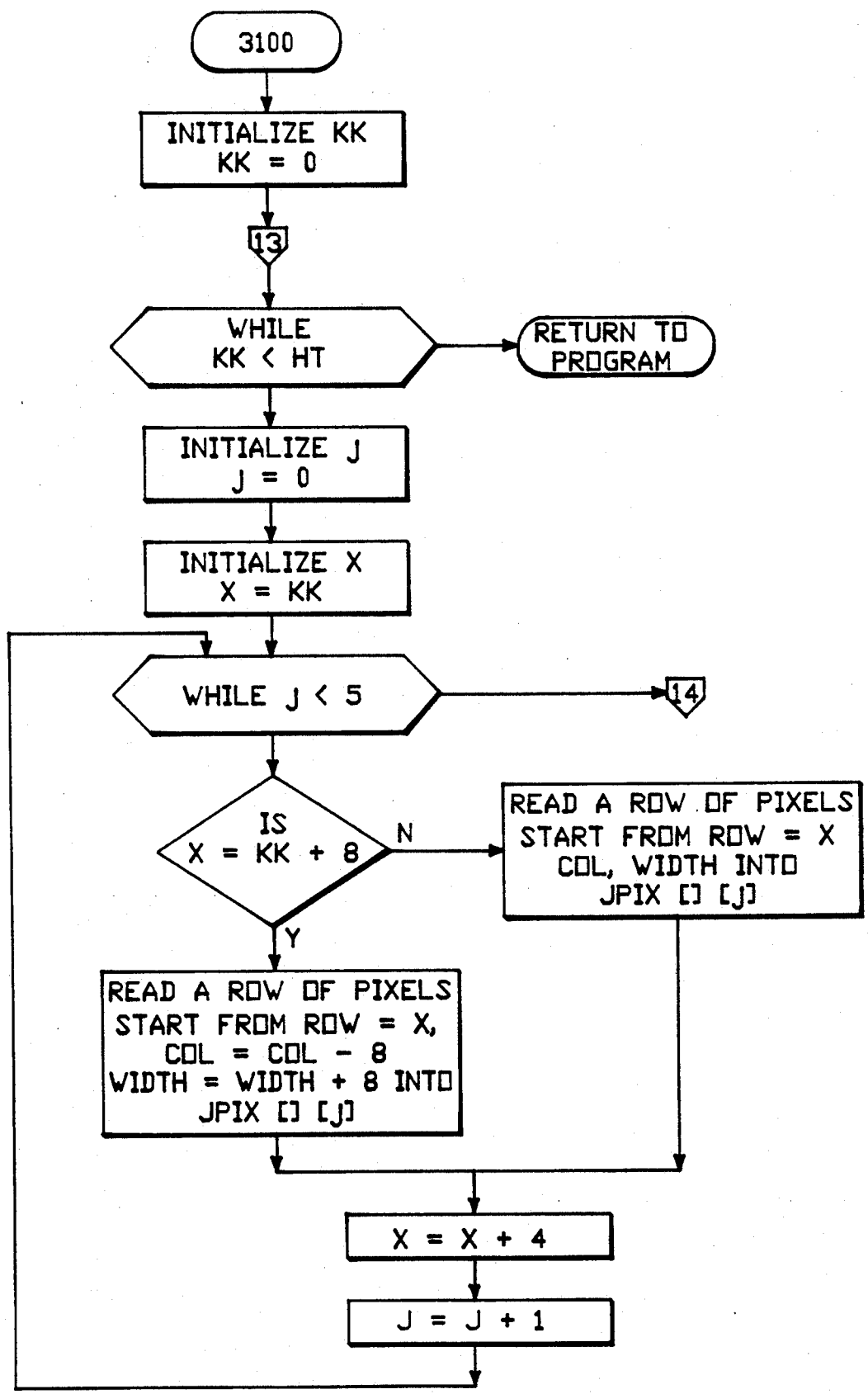
FIG.-4.16

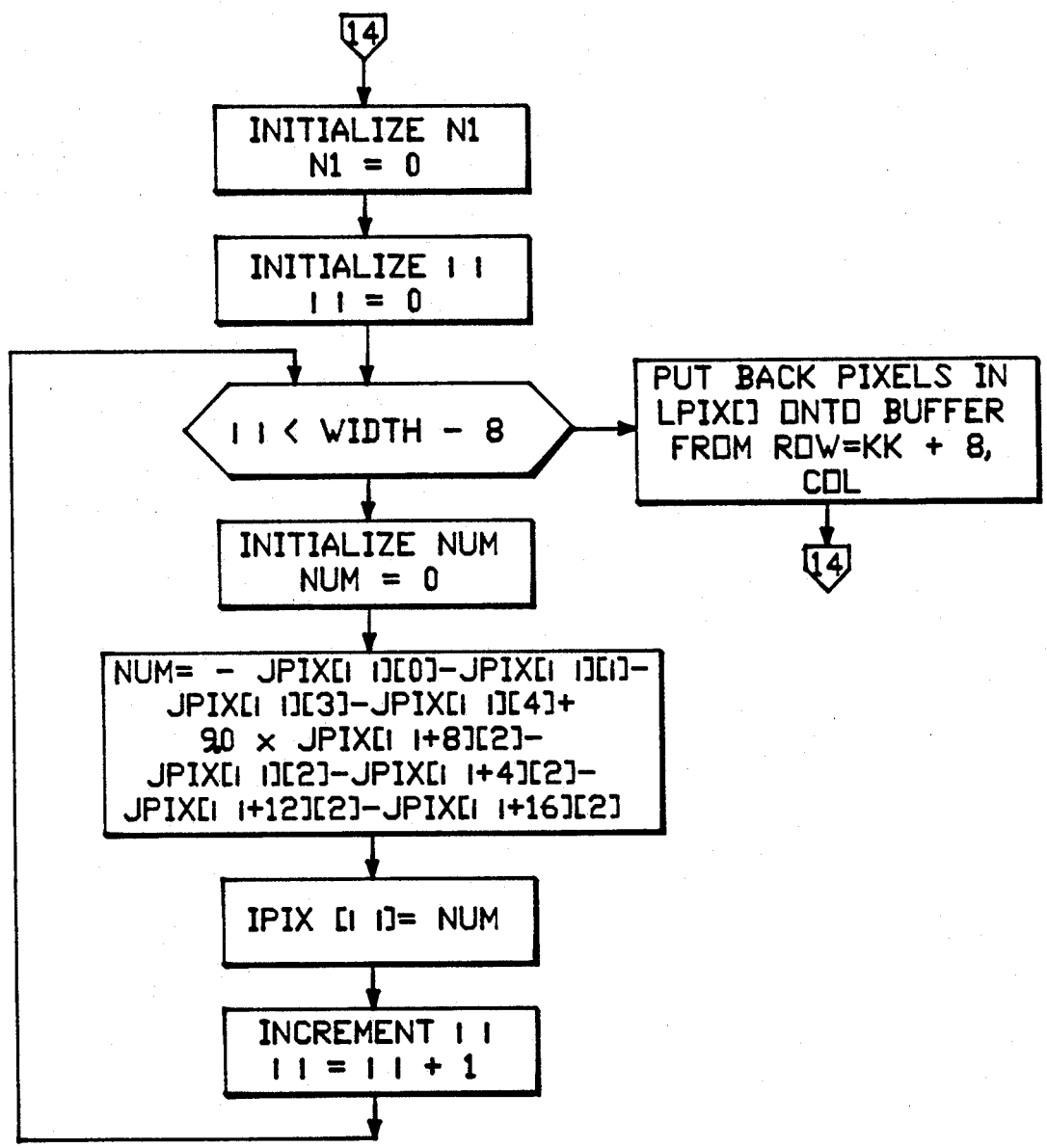
FIG.-4.17

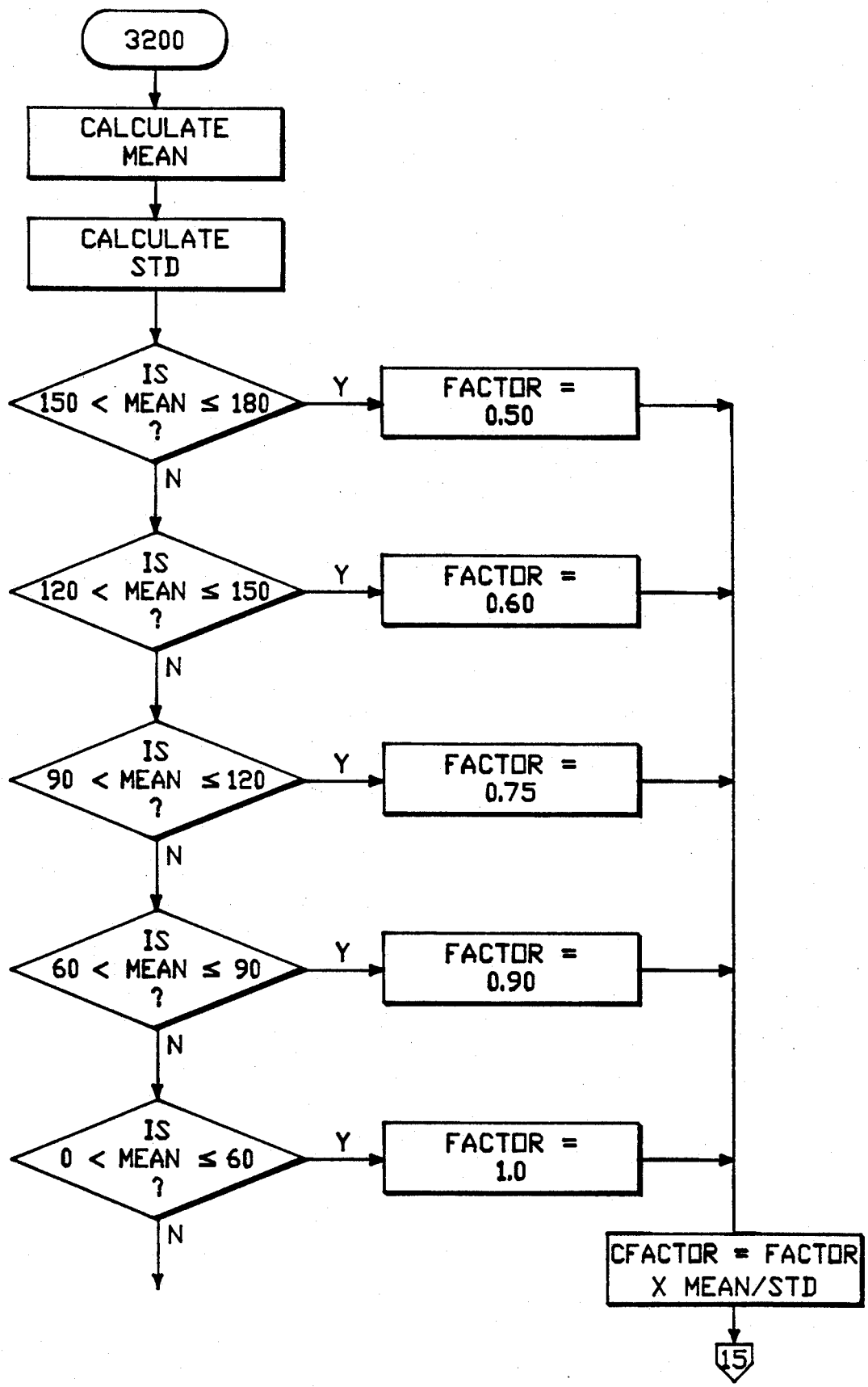
FIG.-4.18

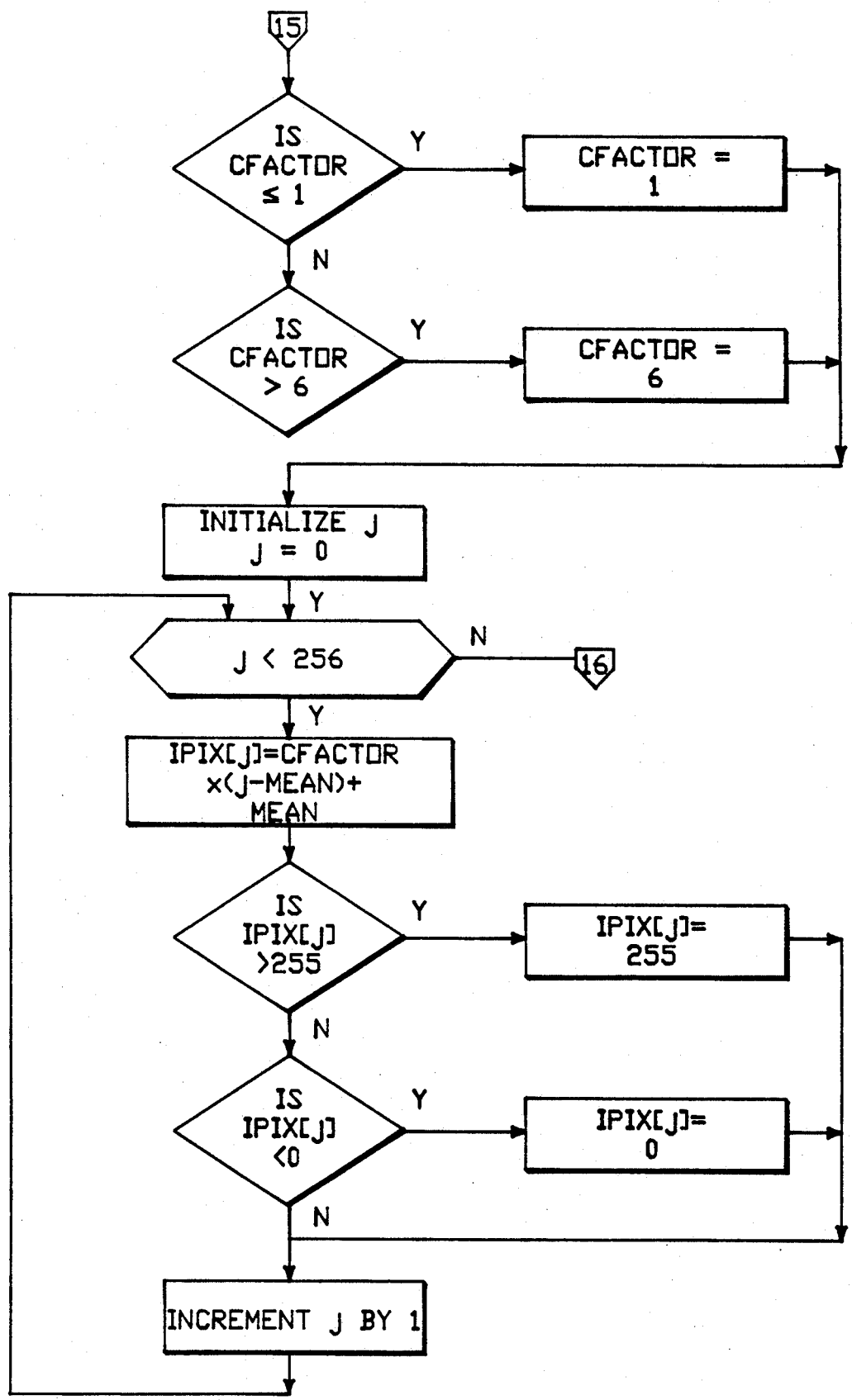
FIG.-4.19

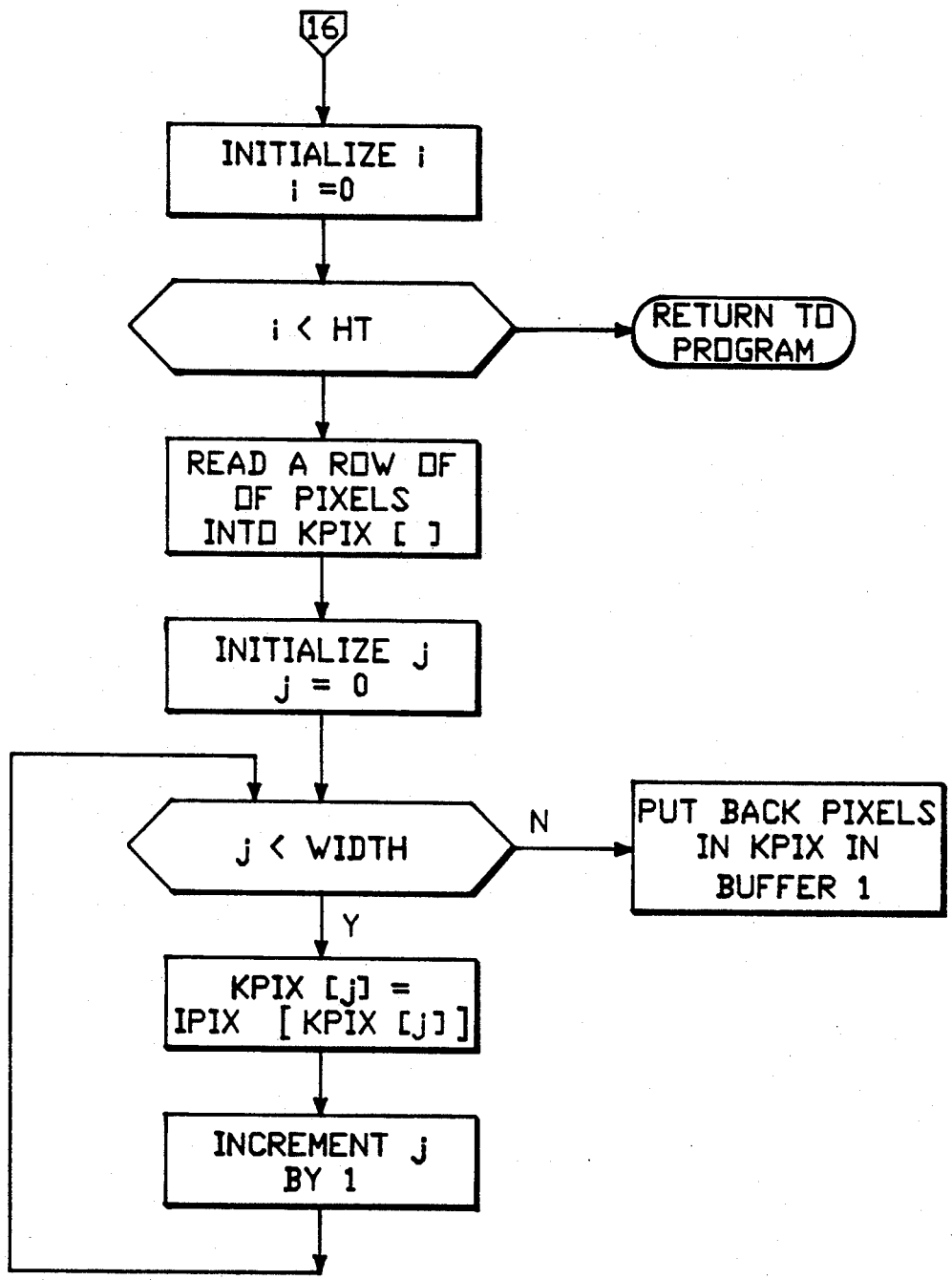
FIG.-4.20

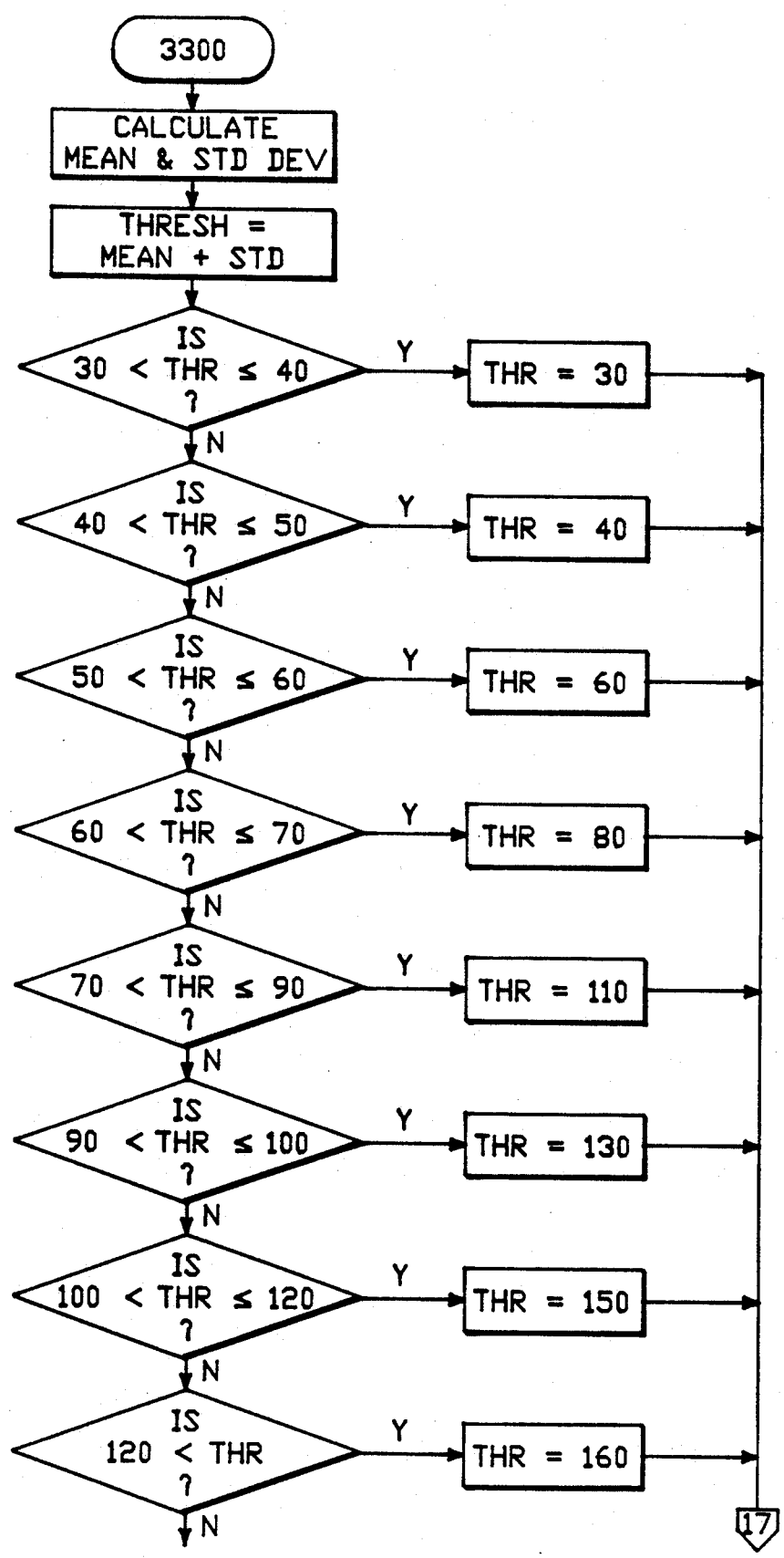
FIG.-4.21

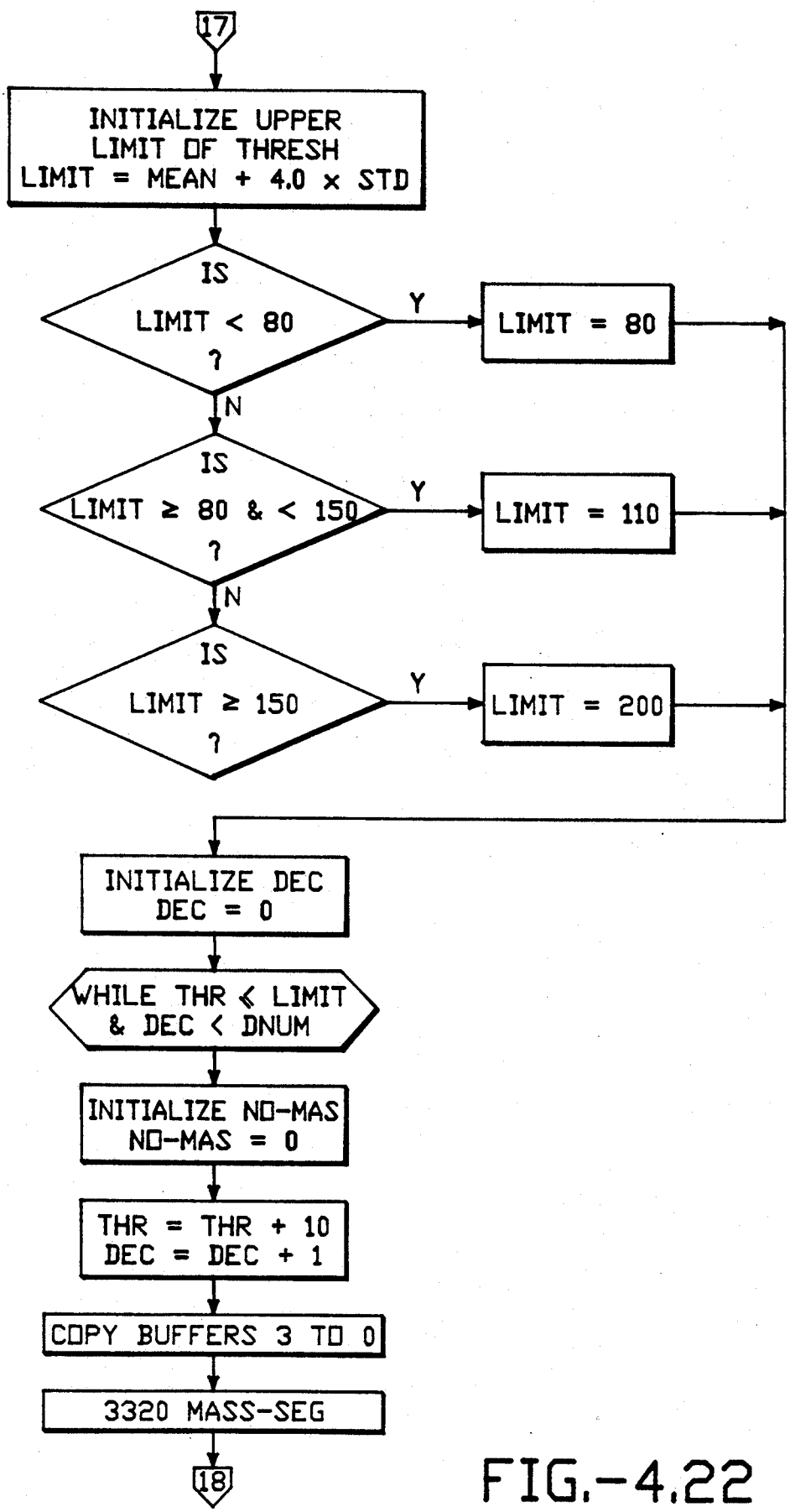
FIG.-4.22

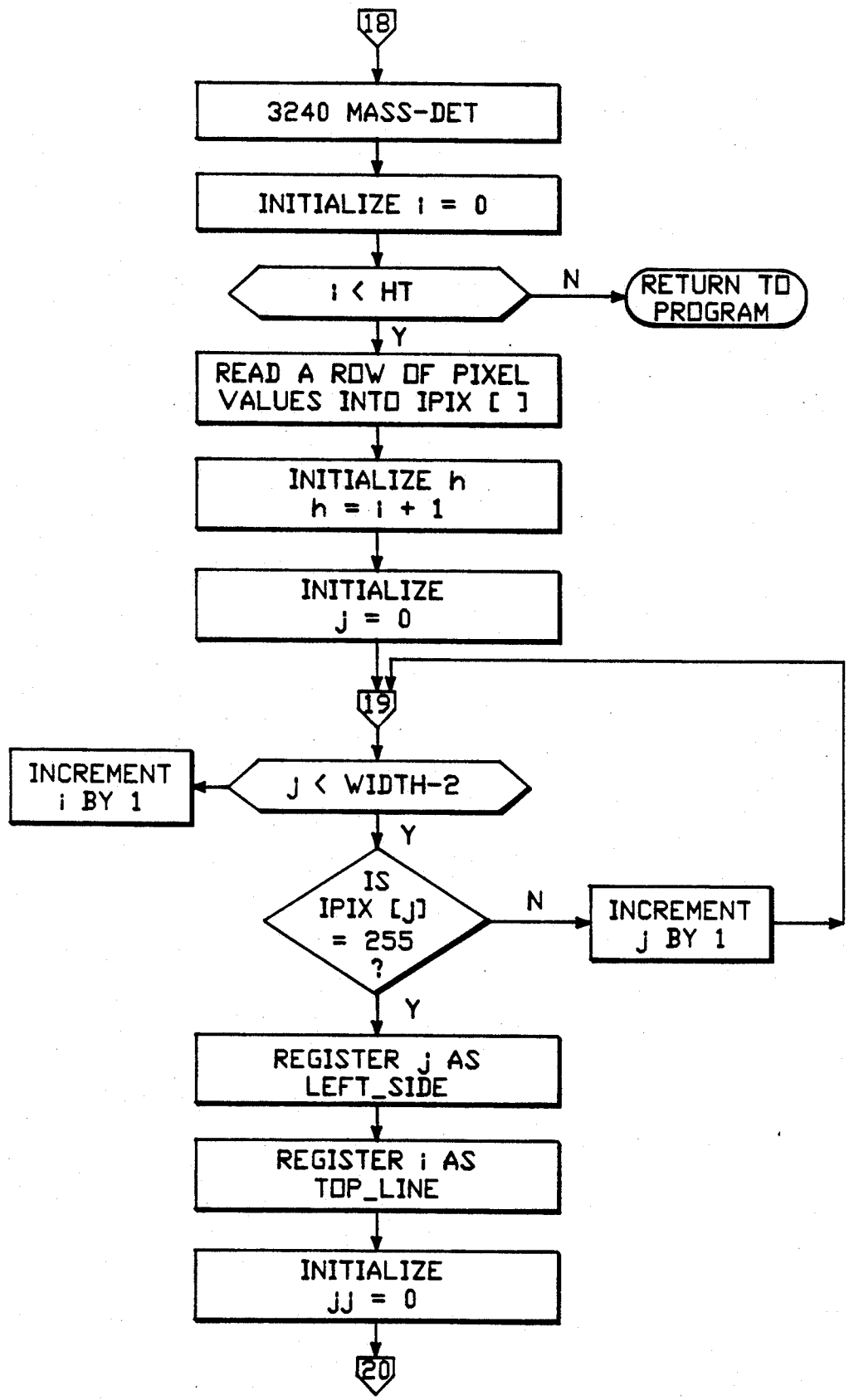
FIG.-4.23

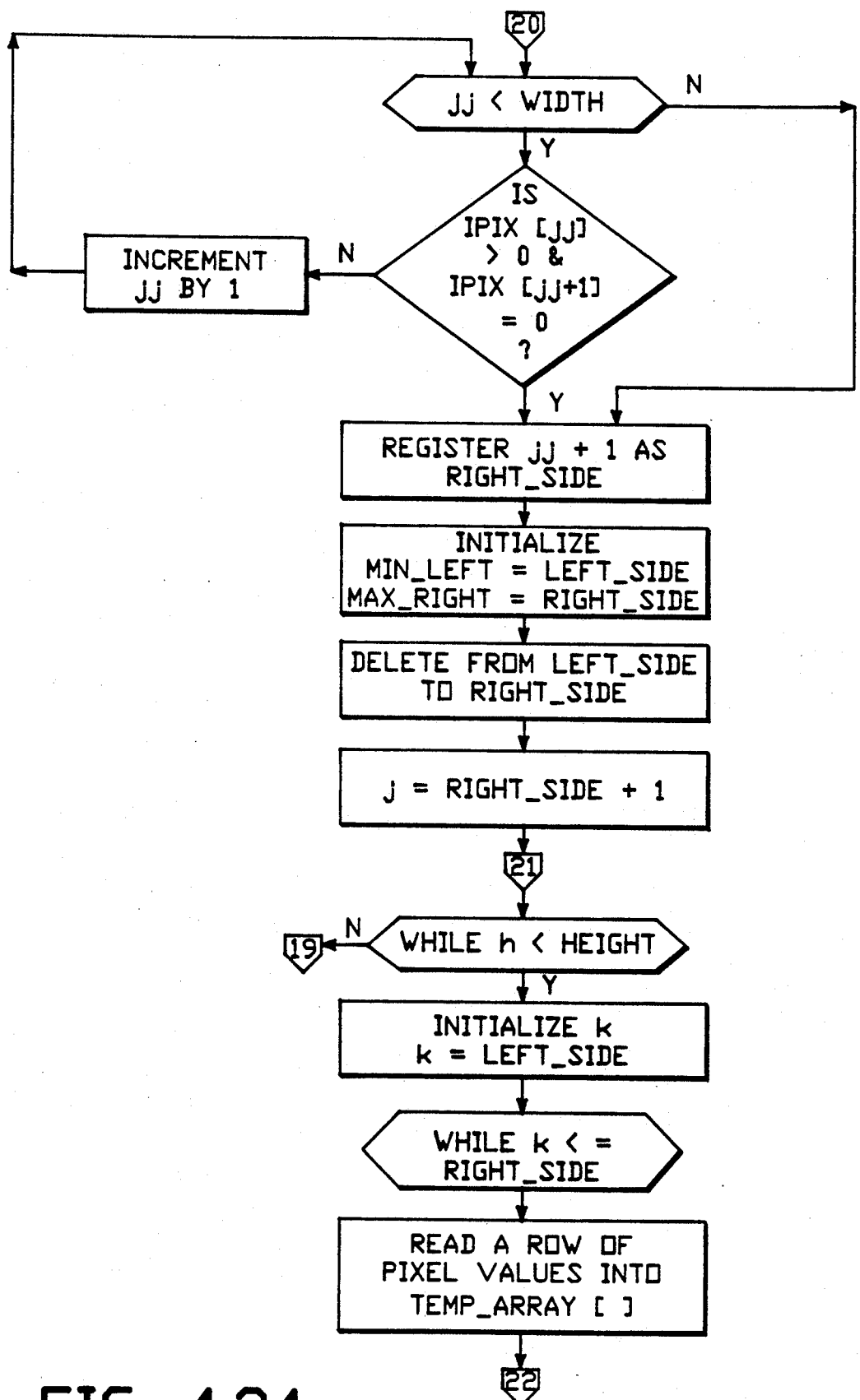
FIG.-4.24

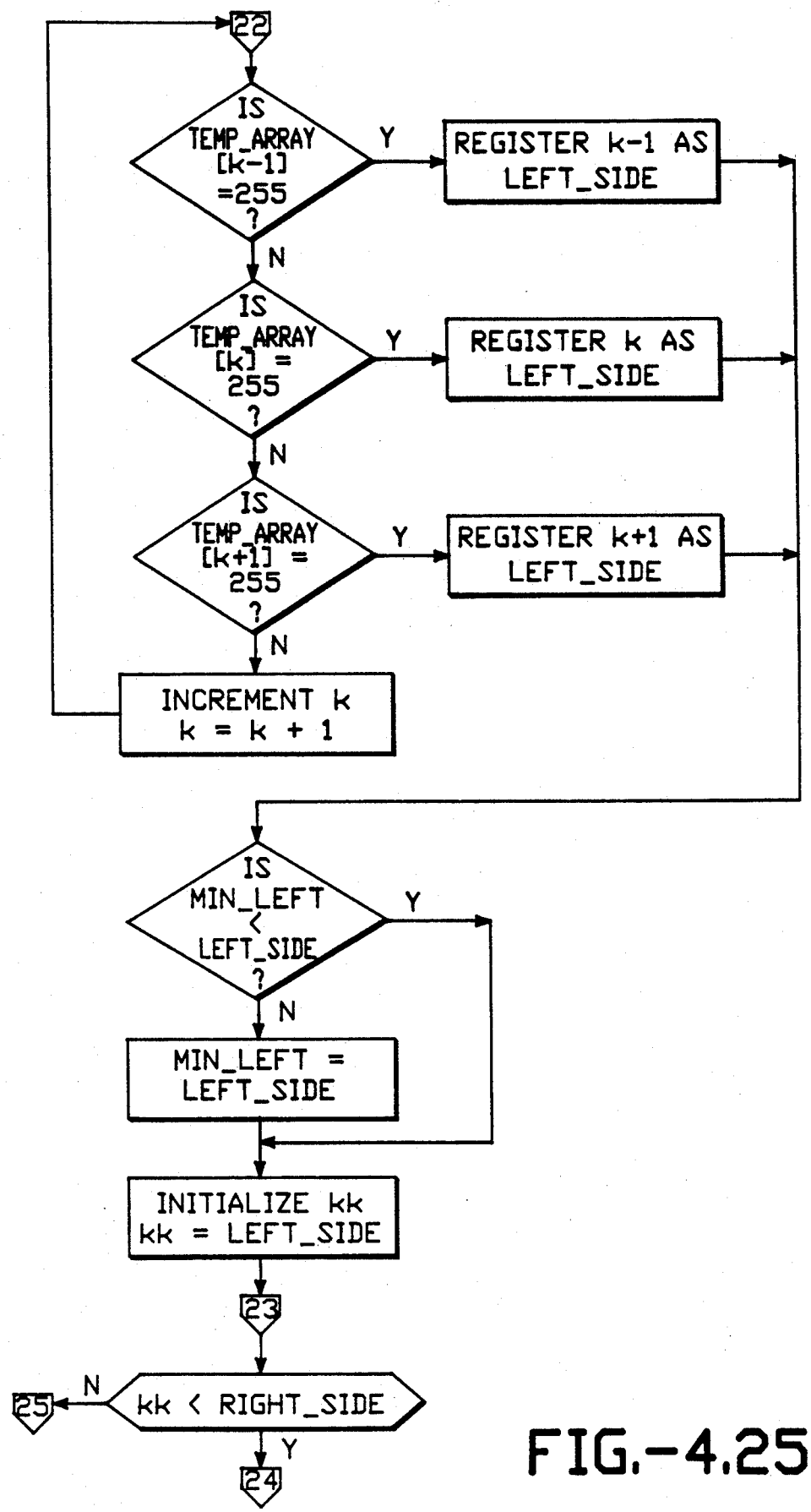
FIG.-4.25

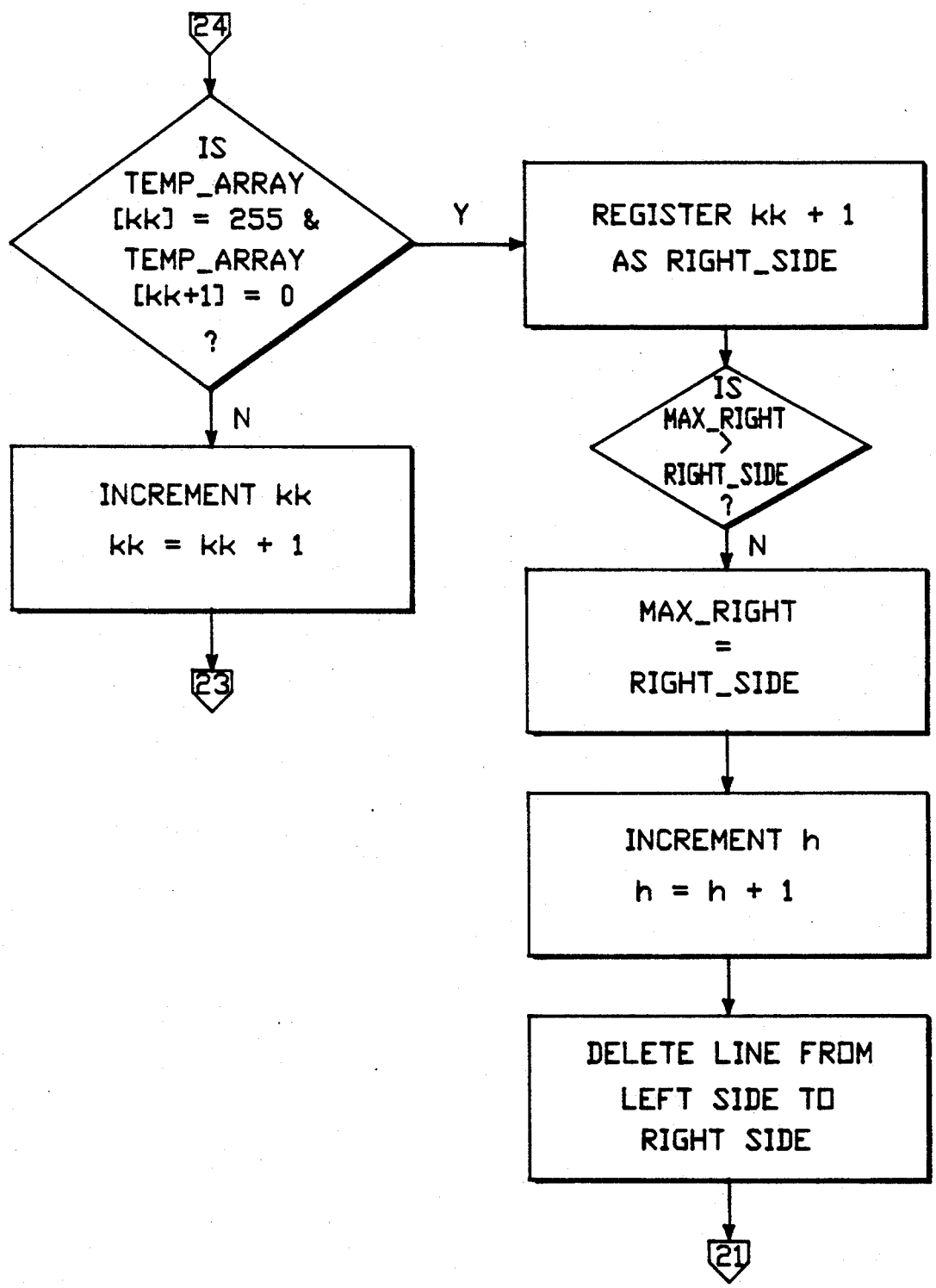
FIG.-4.26

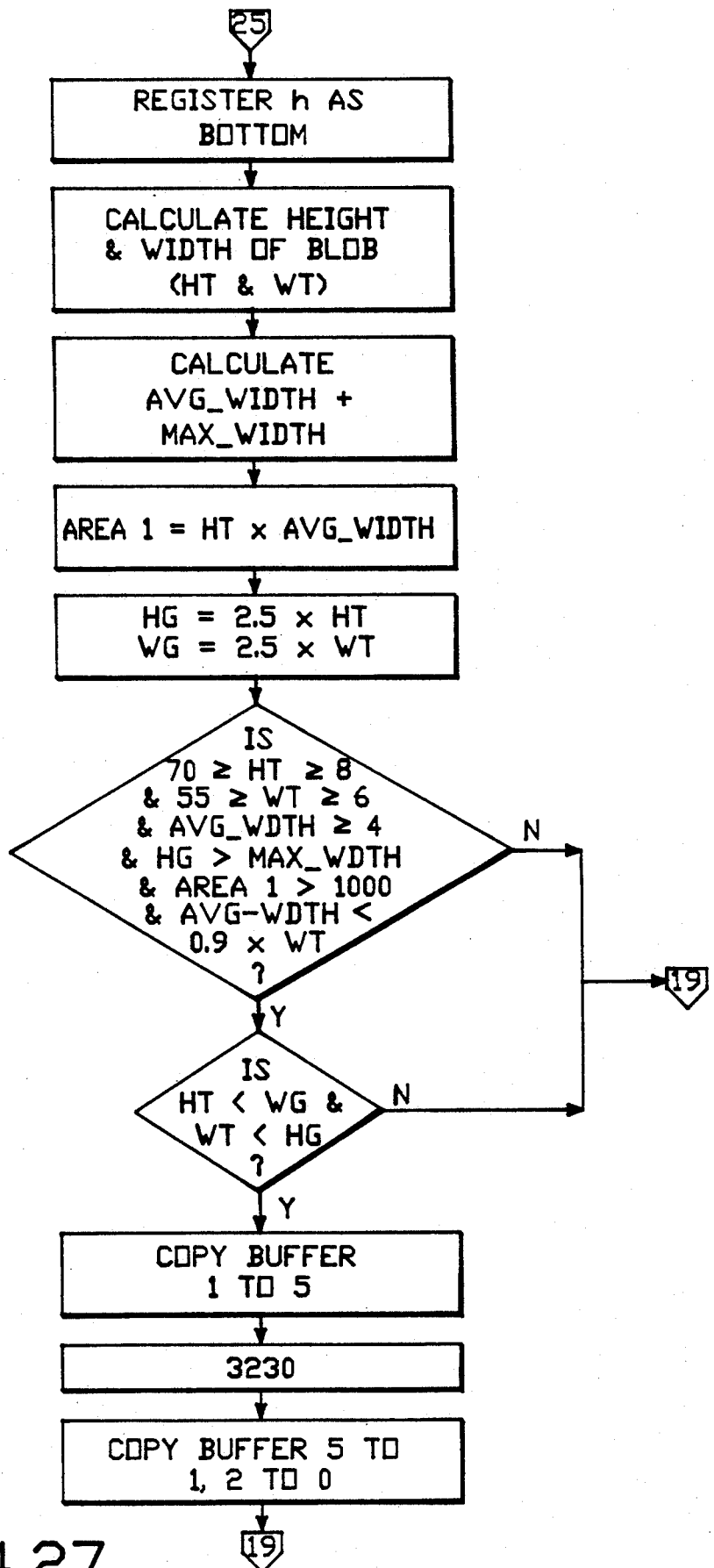
FIG.-4.27

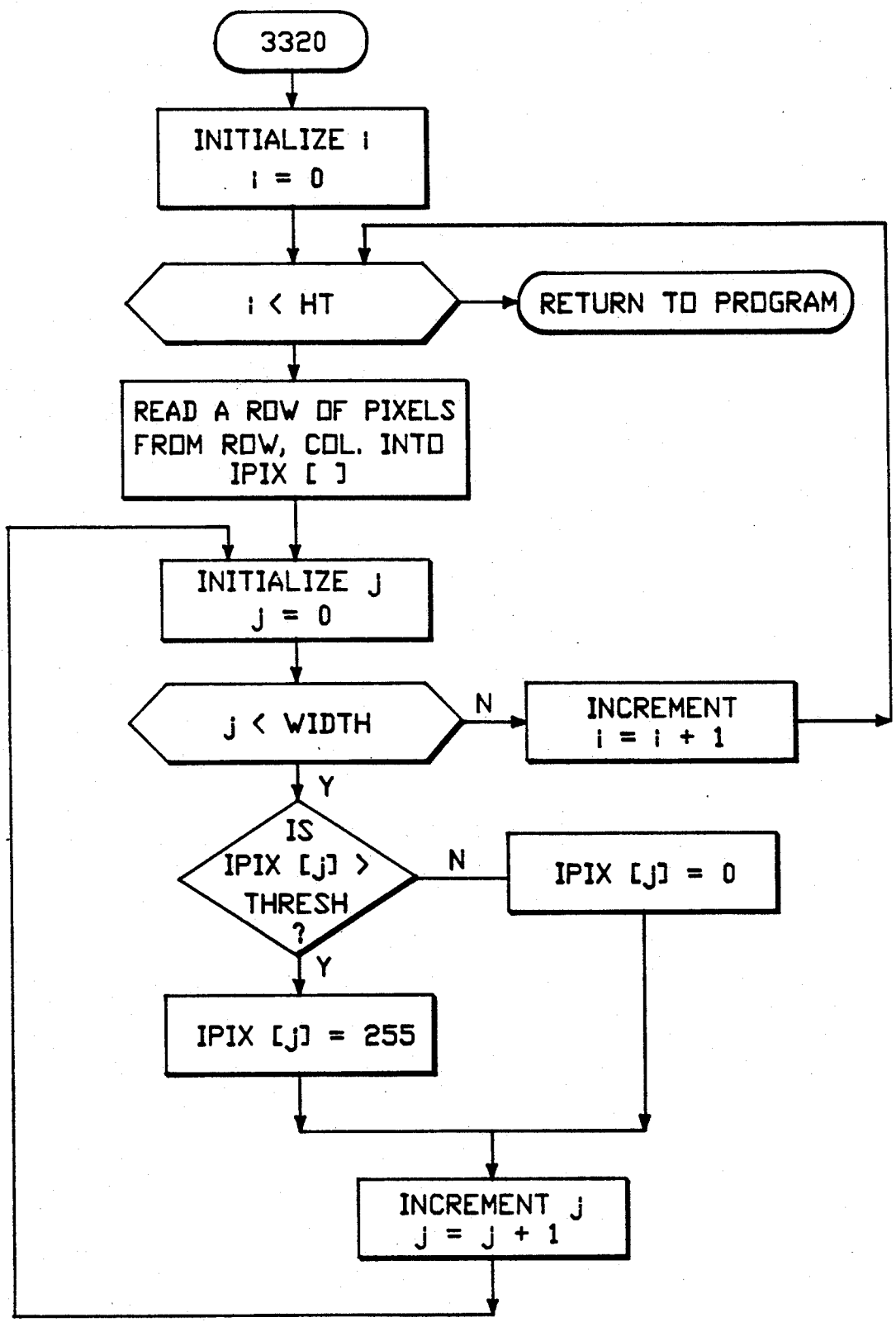
FIG.-4.28

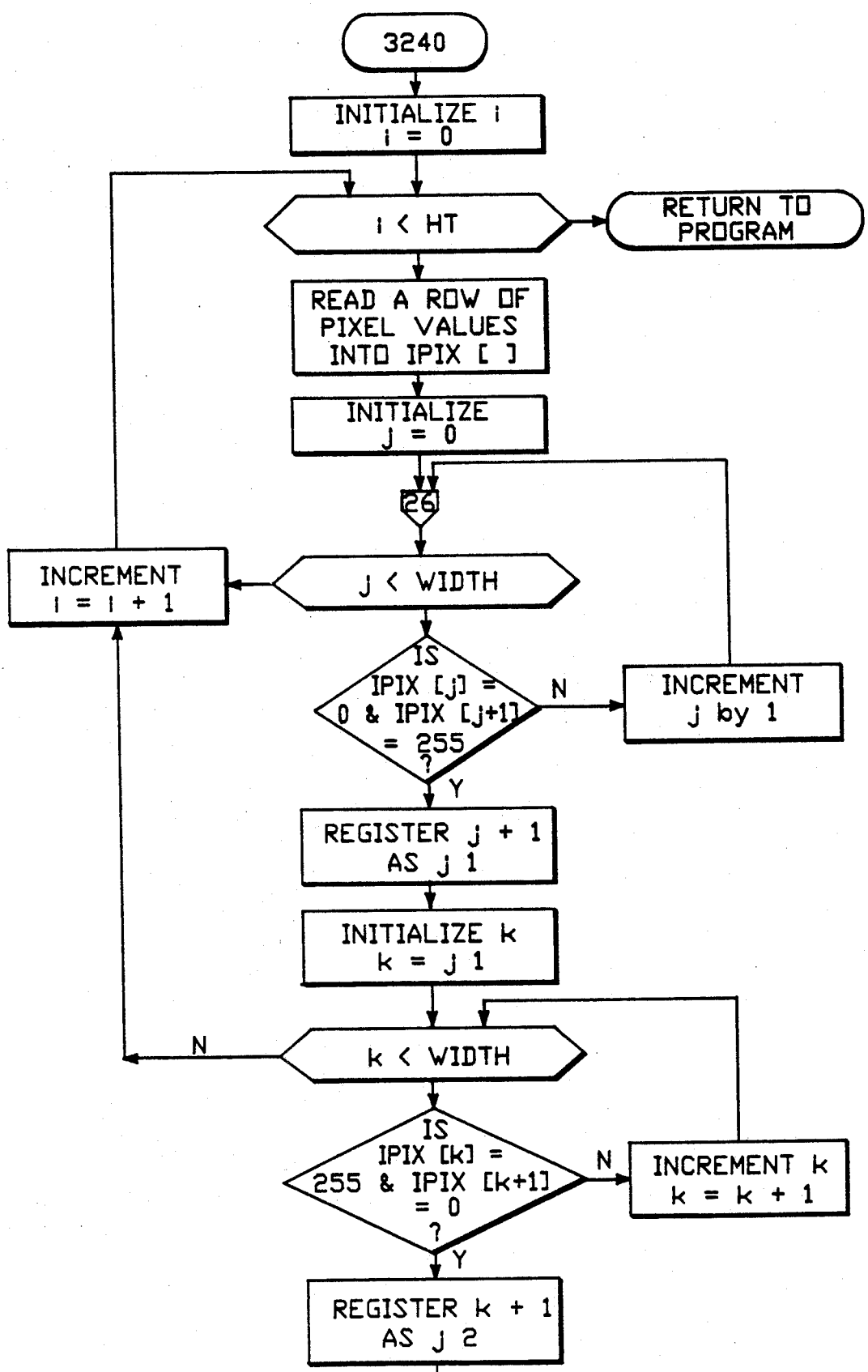
FIG.-4.29

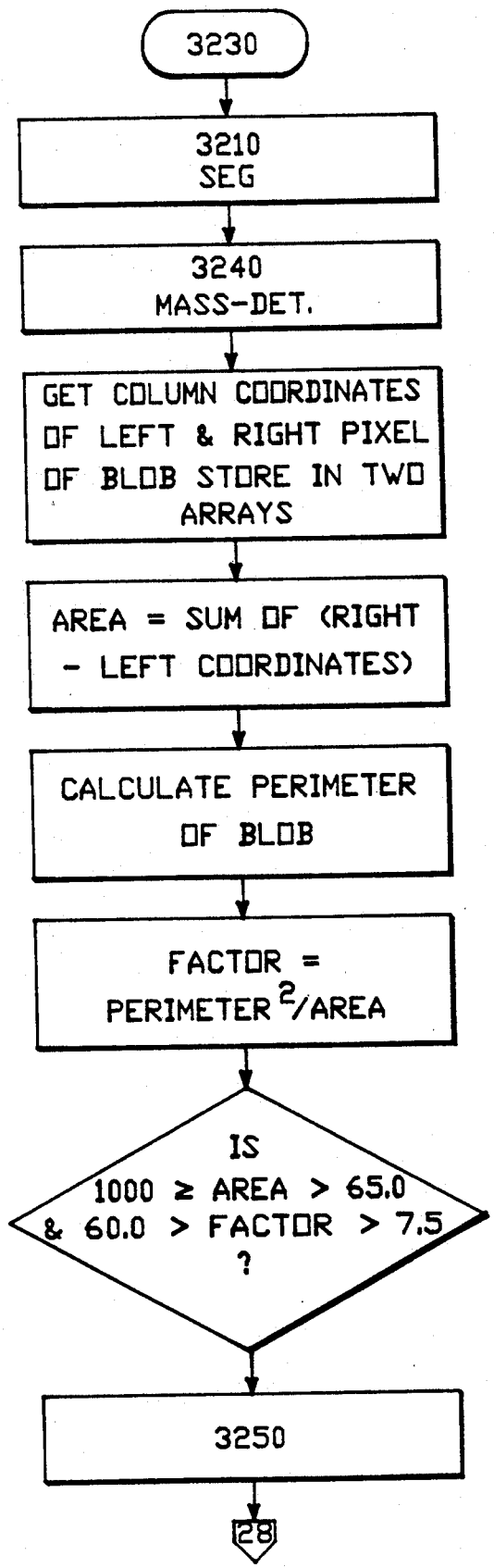
FIG.-4.31

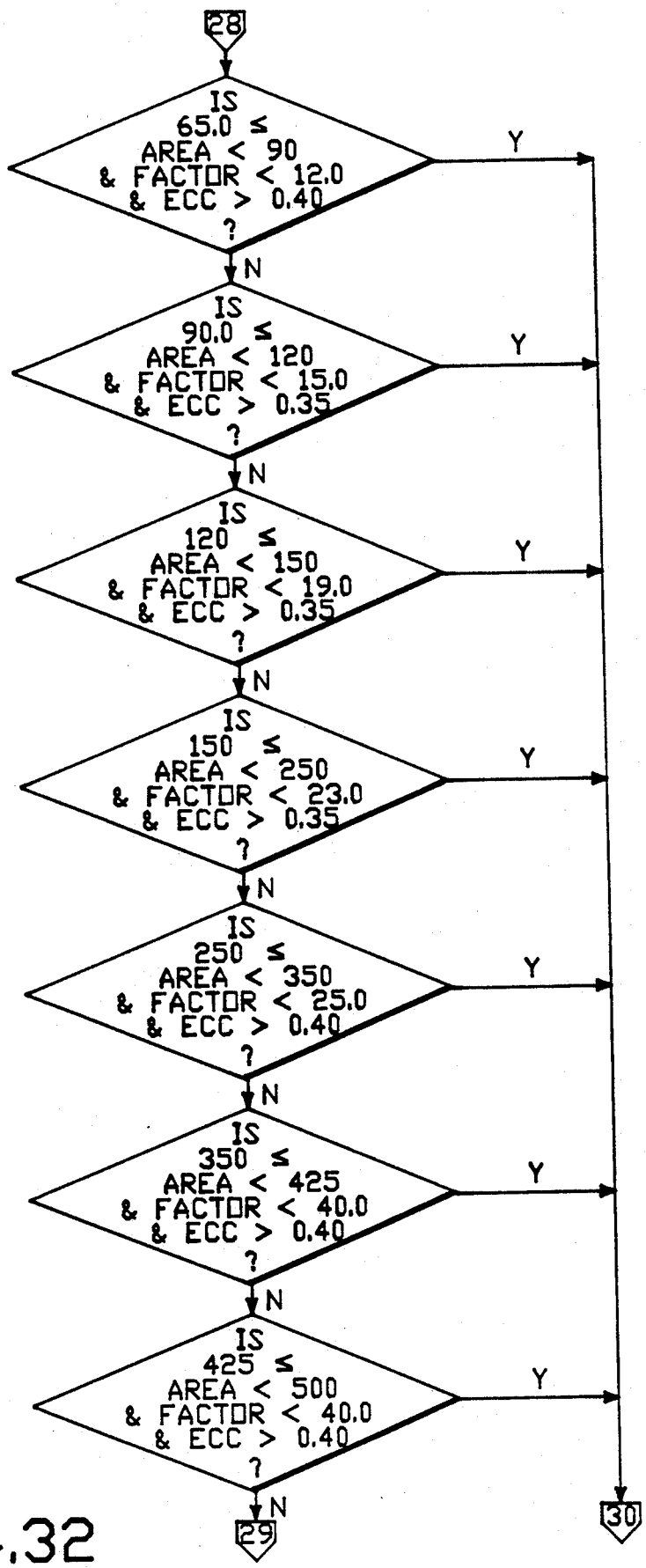
FIG.-4.32

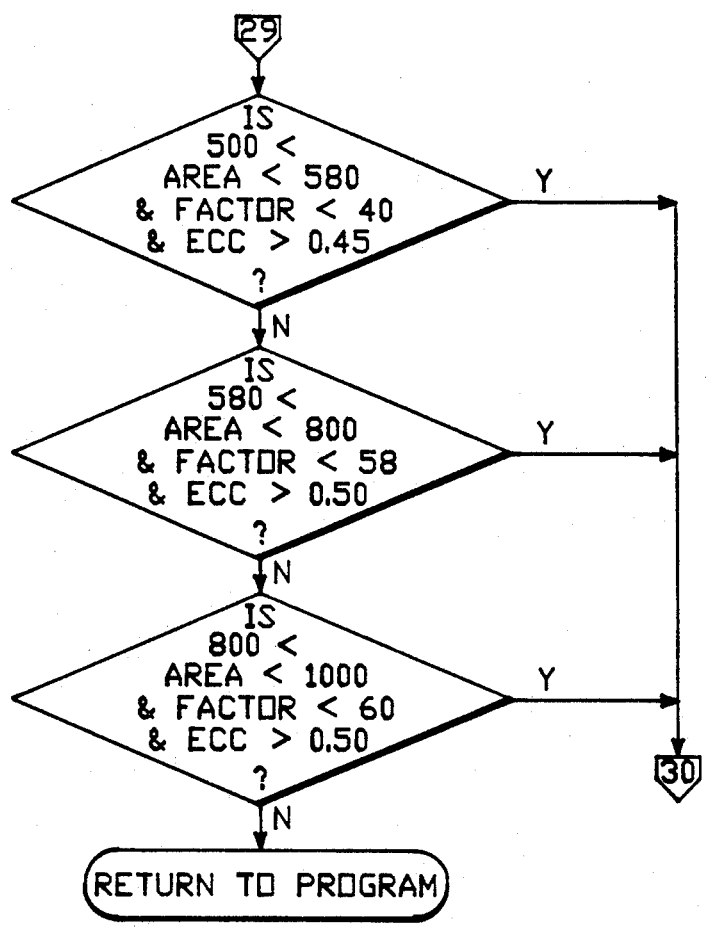
FIG.-4.33
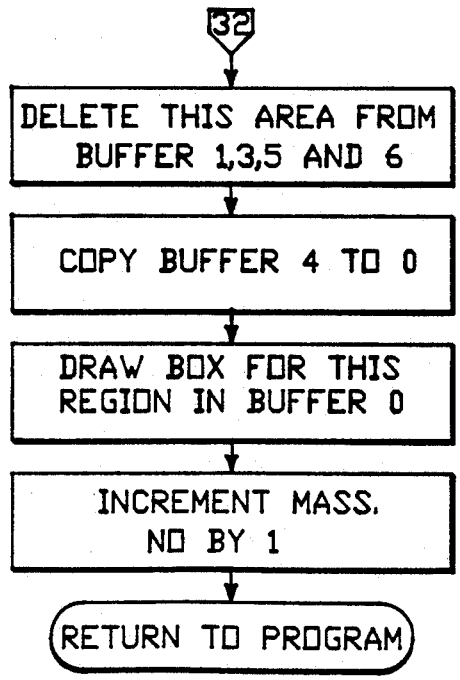
FIG.-4.34

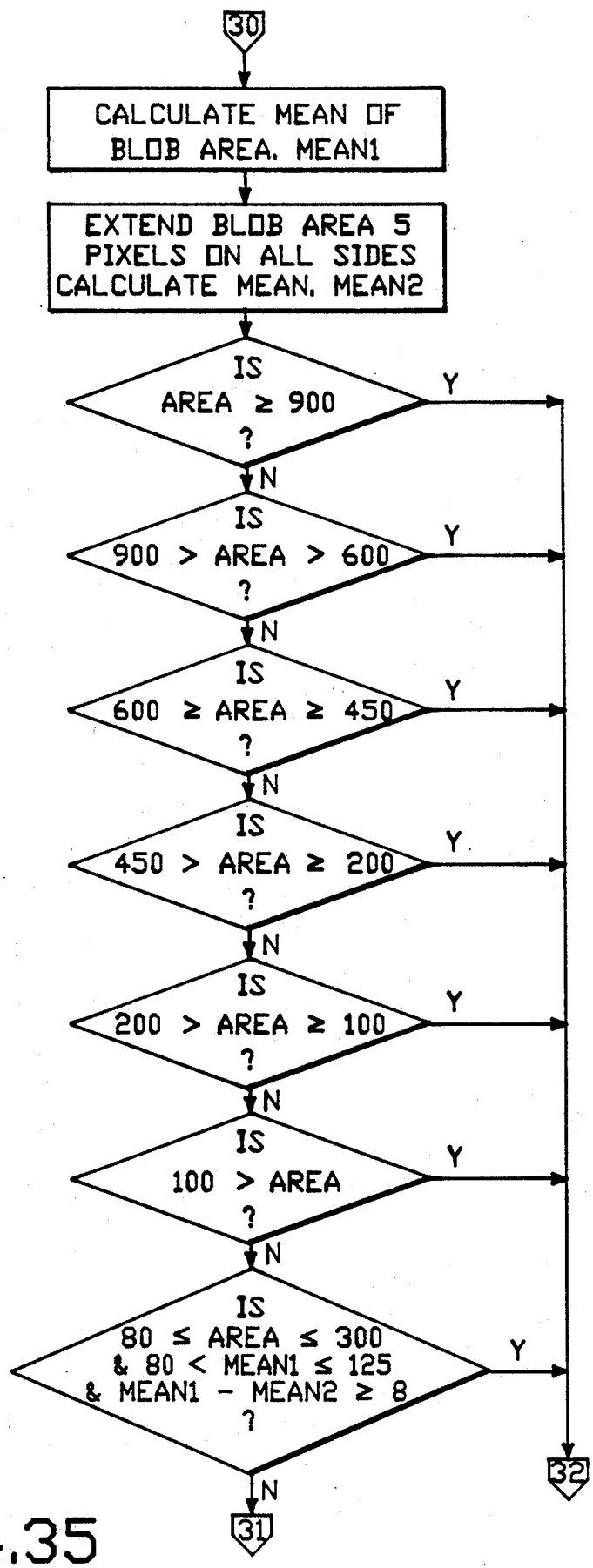
FIG.-4.35

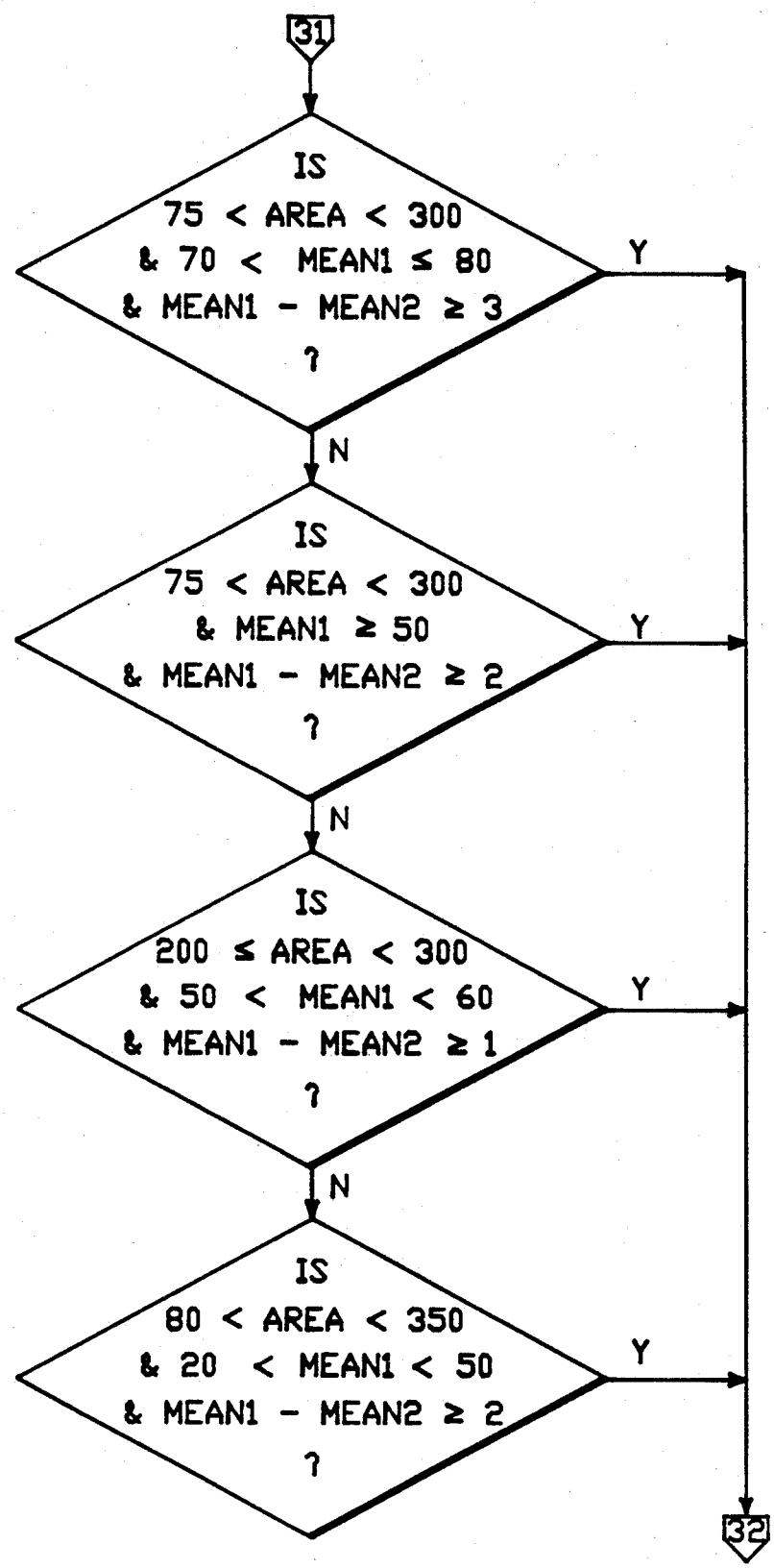
FIG.-4.36

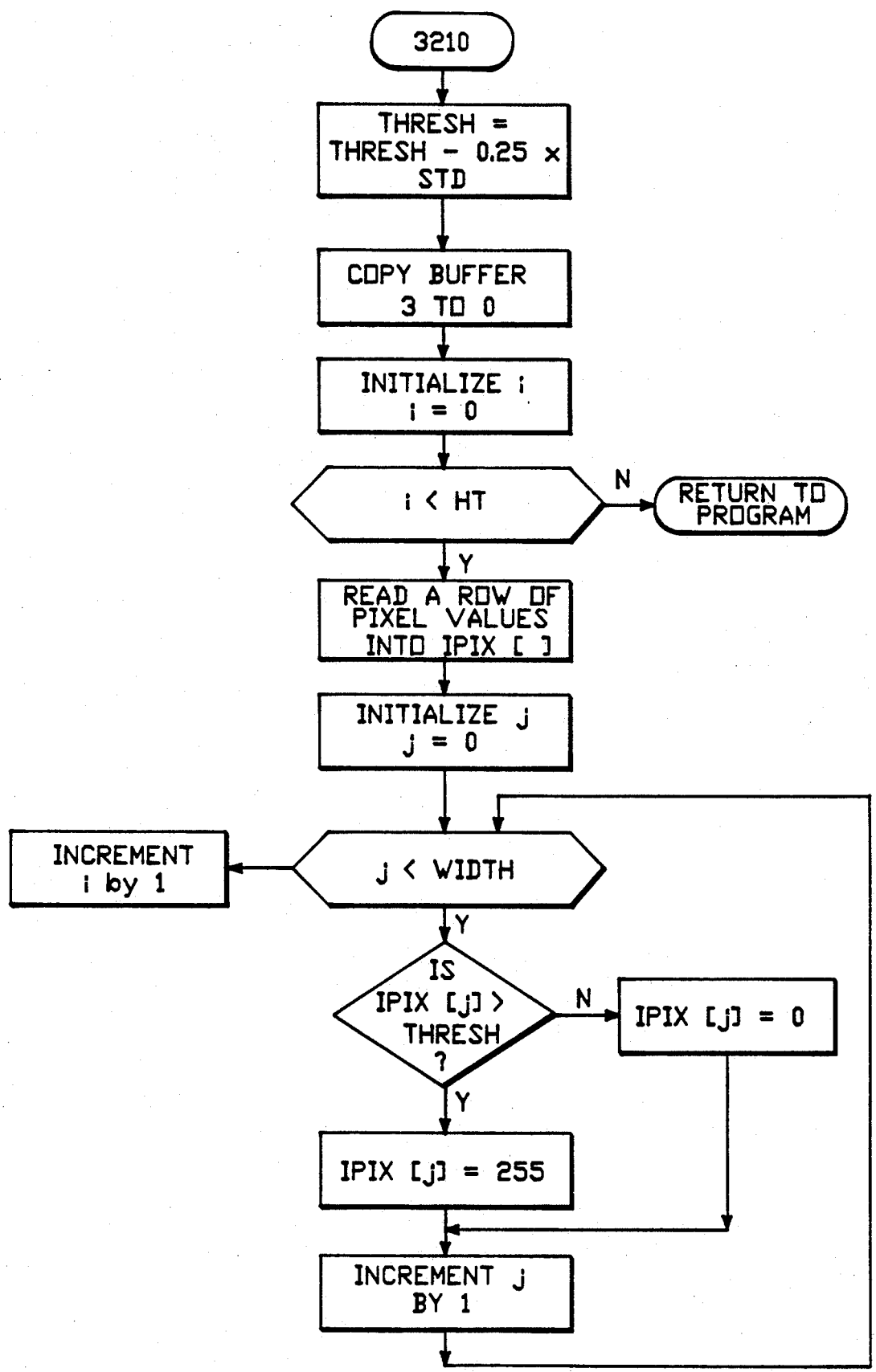
FIG.-4.37

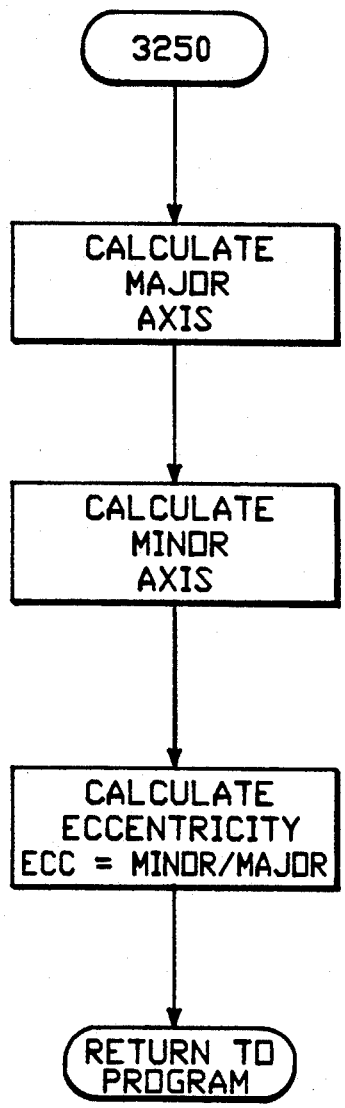
FIG.-4.38

METHOD OF INVESTIGATING MAMMOGRAMS FOR MASSES AND CALCIFICATIONS, AND APPARATUS FOR PRACTICING SUCH METHOD

BACKGROUND OF THE INVENTION

The present invention relates to a method for assisting a physician or other person to investigate a human breast for a malignancy, and apparatus especially adapted to facilitate the investigation of an object for a preselected condition, such as to investigate a human breast for a malignancy.

Mammography is widely used to facilitate the investigation of human breasts for breast cancer. A pair of generally orthogonally related X-rays (called mammograms) are taken of the human breast being checked. These X-rays are then examined by a radiologist or other physician to determine if the mammogram images illustrate any suspicious areas in the breast which should be investigated. In general, the diagnosing party uses a magnifying glass or the like to examine each of the mammograms for suspicious masses (concentrated densities) or calcifications.

Video equipment has been designed in the past to aid in examining mammograms. Such equipment has been relatively limited, though, in capability. For example, most equipment only provides a video image of a mammogram that is an enhanced or magnified view of the same. This enhanced or magnified view can be more easily examined by a radiologist or other physician. However, none to date have been designed which, in essence, identify areas of a mammogram which clearly are of interest. Arrangements have been described in the past designed to aid detection of a specific kind of abnormality in a portion of the human body, including the breast, which is suspicious. For example, reference is made to U.S. Pat. Nos. 4,907,156; 4,323,973; and 4,663,773. However, insofar as applicant is aware, none have developed a method and apparatus specifically designed to locate all major suspicious areas that may be illustrated in a mammogram, nor has anyone developed a method and apparatus taking into consideration the intuitive nature of an expert diagnosis.

SUMMARY OF THE INVENTION

The present invention enables one, such as a radiologist or a physician, to utilize the diagnostic capabilities of experts either to facilitate investigation or to check against the same. Numerical and empirical criteria are developed based on the intuitive criteria used by experienced radiologists in analyzing a mammogram. This preselected criteria is then implemented via a computer program. In essence, the invention applies spatial domain filters for determining the regions within a mammogram having suspicious masses and microcalcifications. (By microcalcification is meant a calcification which may not be sufficiently large in-of-itself to be noticed visually.) The invention includes optically analyzing a mammogram to acquire information defining a characteristic, thereafter applying preselected criteria to the information to identify those regions of the breast which it is recommended be investigated, i.e., those regions containing the characteristic meeting the criteria, and then displaying such regions. The criteria that is applied to identify the regions of interest can be selected by analyzing the diagnosis provided by a number of experienced radiologists. This analysis will provide information defining the intuitive approach taken by such radiologists. The intuitive diagnostic information is then converted to mathematical criteria and a computer program is prepared to apply the same.

The characteristic of interest typically either is density to learn the presence of a mass (concentrated density) in the breast or the presence of a calcification in the same. The region or regions identified are displayed for use. Most desirably, this display is accomplished by highlighting the region(s) on a visual reconstruction of the mammogram under investigation. A hard copy of the display also is preferably printed out for keeping in the patient's file, etc.

The invention also includes apparatus for assisting the investigation of an object for a preselected condition. To this end, it includes optoelectronic means for acquiring information from an image of the object, a table for positioning the image in the field of view of such means, and a computer for acquiring information from the optoelectronic means identifying a region of the same to be investigated. The image can be a mammogram and the preselected condition can be a characteristic of the illustrated breast meeting preselected criteria. Most desirably, the apparatus includes a zoom lens or the like on the optoelectronic means to change its field of view relative to the location on the table at which the image is to be supported. This enables particular sections or regions of the mammogram to be magnified. A display monitor is included as part of the apparatus for displaying not only the magnified portion of the image, but also the full image both with and without the regions in question highlighted.

The present invention includes other features and advantages which will be described or will become apparent from the following more detailed description of a preferred embodiment.

BRIEF DESCRIPTION OF THE DRAWING

With reference to the accompanying drawings.

DETAILED DESCRIPTION OF PREFERRED EMBODIMENTS OF THE INVENTION

Figure 1:
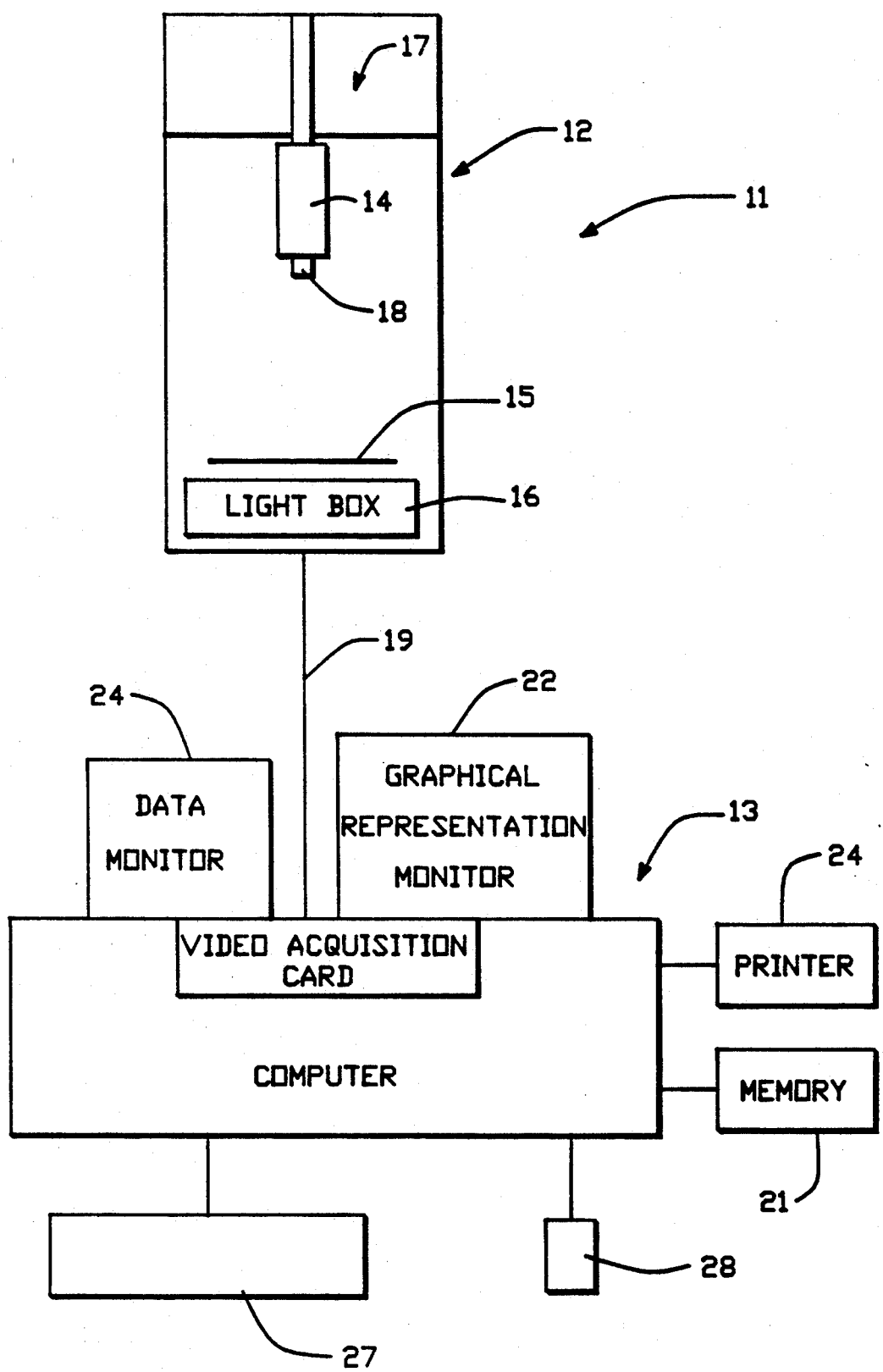
FIG. 1 is a diagrammatic view of a preferred embodiment of the apparatus of the invention.

A preferred embodiment of the apparatus of the present invention is generally referred to by the reference numeral 11 in the diagrammatic view of FIG. 1. Such apparatus includes optical subassembly 12 and microcomputer subassembly 13. These subassemblies 12 and 13 respectively extract information from a mammogram and process such information.

Subassembly 12 preferably is housed within a cabinet as illustrated. It includes optoelectronic means for acquiring information from an image of an object, such as a mammogram. Most simply, such means is implemented in this preferred embodiment by a camera 14. This camera is desirably a CCD video camera of the type designed to acquire images for quantitative image analyses. In one implementation of the present invention, the camera is Model 4810 sold by Cohu, Inc. of San Diego, Calif. A table 15 is provided for positioning the image in the field of view of camera 14. In this connection, a light box 16 is most desirably included as part of the subassembly 12 to illuminate the image. If the image is an X-ray film, e.g., a mammogram, it will be appreciated that the light box will provide illumination which highlights the same.

Camera 14 is suspended within the cabinet by a standard x,y,z positioning system schematically represented at 17. Such system enables one to move the camera as desired to adjust the same relative to the image. That is, the location defined by the table 15 for the X-ray is planar, and the position of the camera is adjustable in a plane generally parallel to the plane of such location and toward and away from the same. Such adjustment enables one to select particular areas of a film to be within the field of view of the camera. Camera 14 also most desirably has a zoom lens 18 for picking up the image. Such lens allows the field of view of the camera to be selectively increased or decreased to provide a magnified (or reduced in size) view of a portion of the mammogram. Most desirably, the lens is selected to provide a magnification of at least eight times.

The data or information acquired by the video camera is fed, as is represented by the line 19, to the microcomputer subassembly 13. Such subassembly includes a video acquisition card 20 to receive such data from the camera 14 and translate it into appropriate digital information. In other words, a digital representation of the mammogram, or portion thereof, is generated. It will, in essence, also define the view provided by the camera 14 in a geometric coordinate system defined by grid points.

The microcomputer further will include a central processing unit and the internal memory typically provided for using the same. It is programmed to practice the invention. A suitable microcomputer is the 386 model sold by Televideo, having the 80386 processor chip. The microcomputer subassembly also includes additional memory as represented at 21 in the figure. A portion of this memory preferably is archival in nature and, in this connection, can be magnetic tape and an appropriate drive for the same.

Means are also provided for displaying the results of the computation. Such means includes a graphics monitor 22 for visually displaying the same as will be described. It also includes a text monitor 23 to enable a visual display of the command means. A printer 24 is also provided as part of the display to enable one to obtain a hard copy of any visual display on monitor 22.

The microcomputer subassembly 13 also includes standard input peripherals, such as a keyboard represented at 27 and a mouse 28 to enable the input of data and the selection of various operations and outputs.

In mammography, four different X-ray mammograms are usually obtained for each patient, two of each breast. One of these views is a plan view referred to as a craniocaudal view. A side view also is taken. This view is simply referred to as a lateral view. Thus, each patient will have left craniocaudal and lateral mammograms, as well as right craniocaudal and lateral mammograms.

Figure 2A:
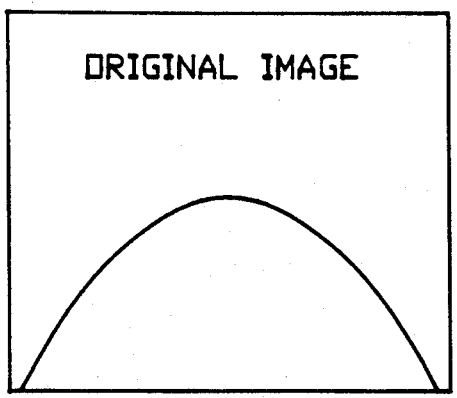
FIGS. 2(A)–2(F) are different schematic views of visual displays which can be obtained with the preferred embodiment of the present invention illustrated in FIG. 1.

One practicing the invention preferably is first prompted to enter into the computer via the keyboard, identifying indicia for the patient for whom the mammogram information is to be entered. The computer allots locations in hard disk memory to such patient and creates a subdirectory for the patient. The user is then prompted to insert the mammogram that is to be processed, position the camera so that the entire region of the breast is displayed on the graphics monitor (the latter is connected to automatically provide a real-time image of the material picked-up by the camera 14). Camera 14 is positioned by the user via the x,y,z positioning support 17 and the zoom lens 18, if necessary, to obtain a full frame reconstruction on the monitor of the mammogram. The camera is focused to obtain a sharp image and its iris is adjusted to provide the desired brightness of the visual display. FIG. 2(A) is a showing of the visual display at this time.

It should be noted that it is not unusual for a mammogram to include areas of a body or other extraneous matters beside the desired image of a breast. These areas can be deleted either by being covered on the original mammogram or by providing appropriate programming to enable the same to be deleted.

When a user is acquiring information for a particular patient, the above procedure is repeated for the remaining three mammograms.

Once the information defined by a mammogram is acquired by the computer, it applies preselected criteria to the same to identify those regions of the breast which it is believed warrant serious investigation. That is, the computer compares the gray scale levels at the various locations in the breast against background gray scale levels to identify concentrated densities which more than likely represent masses which should be investigated.

Figure 2B:
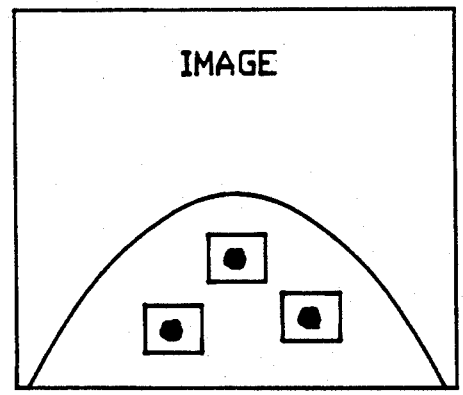

In this connection, such concentrated densities will be significantly more bright (have a higher gray scale level) than the background. The densities which are so identified are then highlighted. The shape of the masses is also taken into account as will be described below in determining which masses are to be highlighted. Any concentrated density providing about five gray scale levels higher brightness than the surrounding background in an area of about 4 mils to 3 centimeters will be highlighted. While the highlighting can be provided in various ways, in keeping with the invention a display of the breast is provided in this embodiment on monitor 22 in which the masses which are identified by the computer have boxes surrounding the same. FIG. 2(B) represents such an image.

Figure 2C:
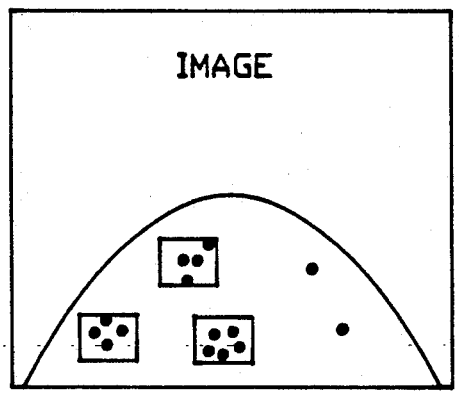

The computer also determines if the formation acquired from a mammogram defines calcifications (or microcalcifications). In this connection, a calcification is significantly brighter than either the background gray scale of a mammogram or of concentrated densities. If a cluster of at least two calcifications is detected in an area of about one square centimeter the region of the same is highlighted. It also can be visually displayed on monitor 22 and FIG. 2(C) illustrates such a view.

Figure 2D:
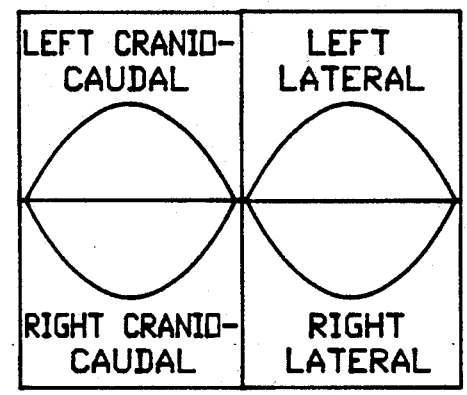

The four mammograms of a particular patient all can be displayed at one time, each in a separate quadrant. FIG. 2(D) illustrates such a compressed view. The two views of the left breast are in the upper half of the display, whereas the two views of the right breast are in the lower half.

Figure 2E:
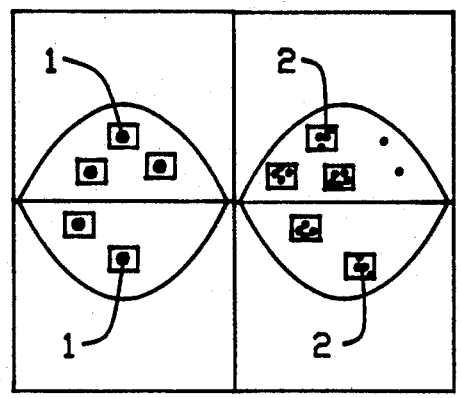

The masses and calcifications detected in the mammograms for the individual breast also can be displayed. FIG. 2(E) shows an example for one of the breasts of a patient. That is, with respect FIG. 2, the two quadrants on the left and right in the upper half of the compressed view illustrate, respectively, the masses and calcifications which have been highlighted with the information acquired from the left craniocaudal mammogram, whereas the two quadrants in the lower half of the view illustrate the masses and calcifications defined by the information acquired from the left lateral mammogram.

Figure 2F:
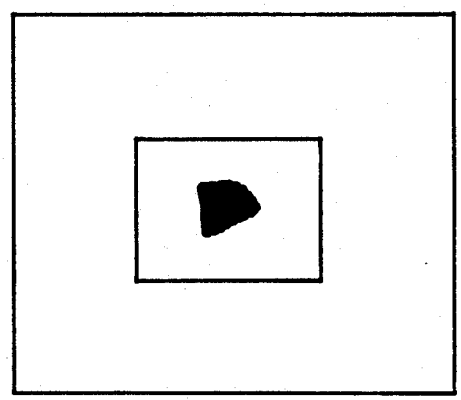

As a particularly salient feature of the present invention, it enables magnification of, for example, a highlighted area. This magnification simply is achieved by using the zoom lens to change the field of view of the camera to coincide with an area selected by, for example, drawing a window about the same with mouse 28. A real-time visual display of the magnified area is placed on the screen of monitor 22. FIG. 2(F) illustrates such a magnification of a highlighted mass. It will be appreciated that such magnification facilitates an investigation by providing more detail then can be seen with the naked eye. Most desirably, digital filters also are applied via the computer to portions of the image in real-time, enhancing sharpness and contrast. Such filtering can be applied to either magnified or unmagnified views to facilitate such examination.

It will be seen from the above that the invention greatly aids a physician's or other person's investigation of a human breast for a malignancy. It not only identifies sites to be investigated in detail, it allows various manipulations, including magnification and enhancement as discussed above, to facilitate such investigation. It also catches matters, particularly microcalcifications, missed in conventional viewing techniques. It can be used to provide a "second opinion" when one wishes to investigate a mammogram in a conventional manner. Printer 24 is connected to provide a hard copy of any particular visual display which is provided on the monitor 22. Such a hard copy can be used, of course, to obtain verifications, opinions, etc. from those incapable of viewing an image on the monitor itself. Moreover, hard copies of the showings in, for example, FIG. 2(E) can be printed to be placed in a patient's file.

Figure 3:
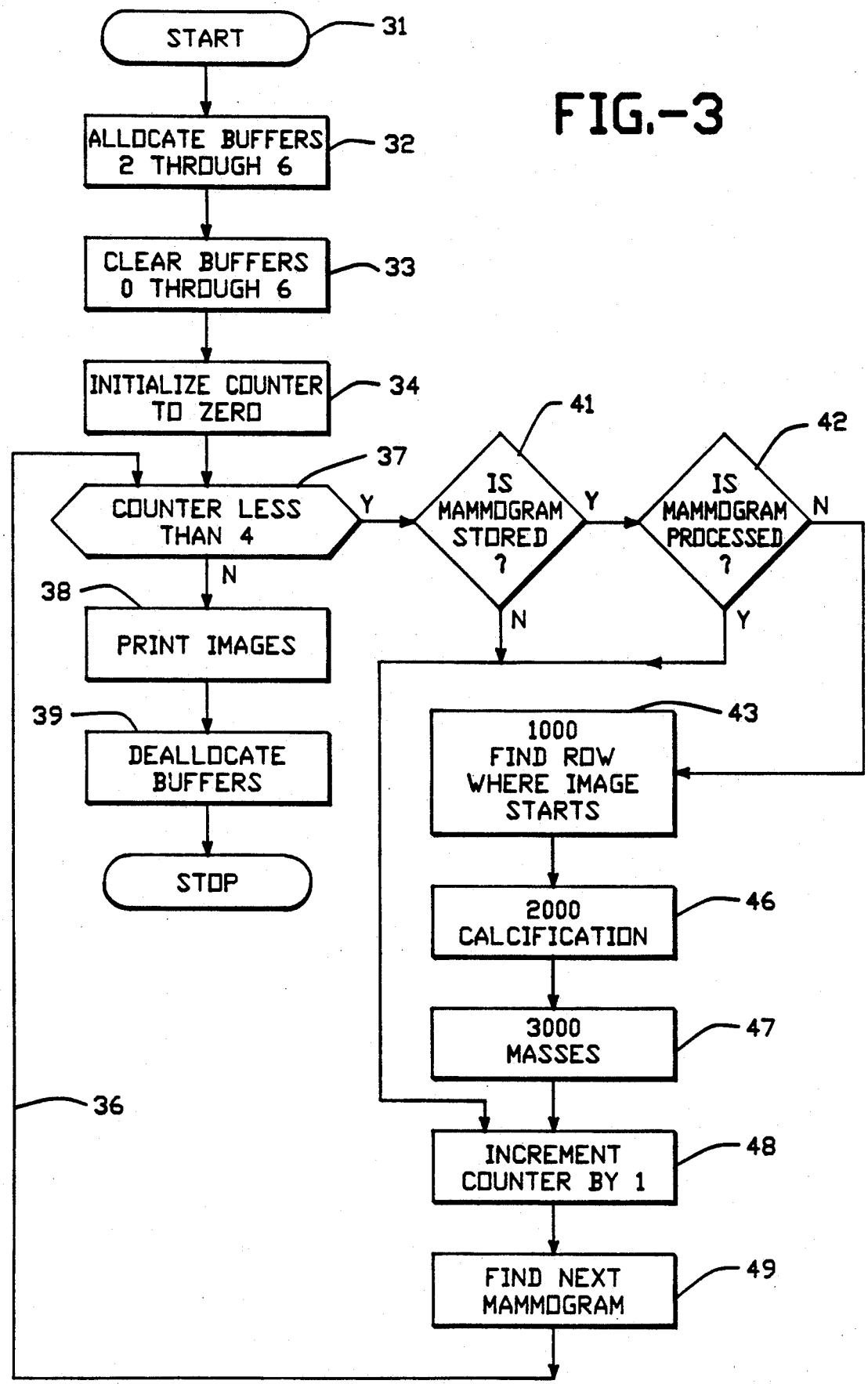
FIG. 3 is a flow chart of a computer program implementing a preferred embodiment of the present invention.

The flow chart of FIG. 3 is a high level definition of a computer program for implementing the processing of the present invention. It illustrates the steps involved in identifying the location of various calcifications and masses relative to the remainder of such mammographic images.

Initiation of the program is represented by "start" block 31. The first operation is to allocate dynamic memory within the microcomputer for five buffers. This is represented by block 32. These buffers, as well as two additional ones already present in the processor needed to carry out the program, are cleared. This operation is represented by block 33, and a counter for the processing is reset to zero as represented by block 34.

The process to be described is repeated once for each of the mammographic images, as will be described. To represent this a loop 36 is illustrated extending from the end of the process to a box 37 labelled "counter less than 4". If the count provided by the counter is greater than 4, the images which are stored in the buffers are printed as indicated at 38. The buffers are then deallocated as indicated by box 39, and the process is stopped. If the counter is four or less, a determination is made as to whether or not there is information defining a mammogram stored in hard disk memory. This decision is represented in FIG. 3 by decision block 41. If the counter is not timed out, the counter is incremented by one.

Figures 4, 5, 6, 7, 8, 9, 10, 11, 12, 13, 14, 15, 16, 17, 18, 19, 20, 21, 22, 23, 24, 25, 26, 27, 28, 29, 30:
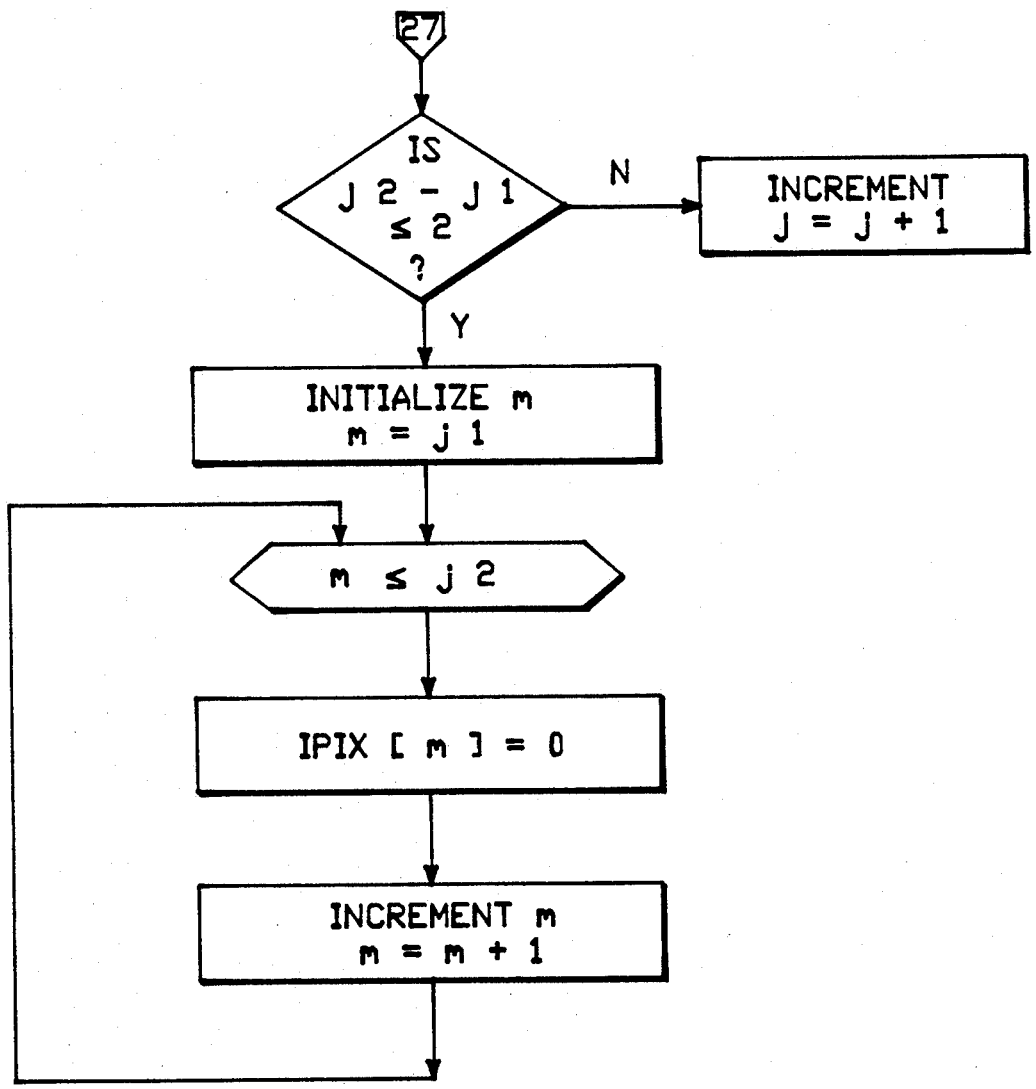
FIGS. 4.1–4.8 are detailed flow charts of subroutines for the program defined by the flow chart of FIG. 3.

If information defining a mammogram is available, a determination is made as to whether or not such information has been processed. If it has, the counter is again incremented by one. If it is not, though, it is processed. Block 42 in the flow chart represents this decision. If it has not been processed, the subroutine illustrated in FIG. 4 and indicated by the numeral 1000 in block 43, is activated to find the row in the mammogram where the image of the breast starts. Once it is located, a section is selected to be investigated. The information defining the image is first investigated to determine if it defines calcifications which should be highlighted. To this end, a subroutine is initiated. This subroutine is represented in the figures by the number 2000 in block 46. It is shown in FIG. 4.2, with other numbers in the 20-hundred range indicating further subroutines.

The mammographic view information being checked is then analyzed to determine if it includes masses which have a greater density than a preselected criteria. This is represented in FIG. 3 by box 47. That is, the subroutines indicated by the 3000 and the decade of 100s above 3000 will be initiated. After the view has been checked for masses, the counter will be incremented by one as represented by box 48, and the other mammographic views are checked in a similar manner (box 49).

The following detailed description is included to assure that one skilled in the art can practice the present invention by designing a program for the detection of both masses and calcifications. It should b noted that terms "image" and "subimage" as used herein at various locations do not necessarily mean an optical image or subimage which is either visually displayed or printed, but rather includes a digital or other representation of such an image or subimage.

DETECTION OF SUSPICIOUS MASSES

Apply the filter described below to the original image, to produce a sharpened image that highlights masses and densities that appear to look like masses (collectively concentrated densities). This kind of filter is known as a spatial domain sharpening filter.

METHOD

Use a square subimage area centered at (x,y), as shown below. Move the center of the subimage from pixel to pixel starting from the top left hand corner, and apply a weighted intensity value sum at each location (x,y) to yield a different intensity value at that location. This weighted sum is given by the formula:

$$T[f(x,y)] = -(f(x-8,y) + f(x-4,y) + f(x+4,y) + f(x+8,y)) + 9.0 \times f(x,y) - (f(x,y-8) + f(x,y-4) + f(x,y+4) + f(x,y+8), \text{etc.}$$

|  |  | (x,y−8) |  |  | $(x-8)^{th}$ row |
|---|---|---|---|---|---|
|  |  | (x,y−4) |  |  | $(x-4)^{th}$ row |
| (x,y−8) | (x,y−4) | (x,y) | (x,y+4) | (x,y−8) | $x^{th}$ row |
|  |  | (x+4,y) |  |  | $(x+4)^{th}$ row |
|  |  | (X+8,y) |  |  | $(x+8)^{th}$ row |

Drawing 1. A 5×5 window showing image pixel location

Partition the image into five sections as shown below, to select areas of uniform intensities.

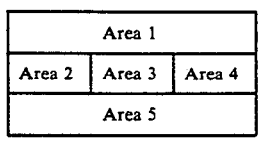

For each of these five sections, do the following:

Apply a medium contrast to further highlight the masses and densities.

Determine the threshold value from the mean and standard deviation of intensities of the original image using the empirical formula given below:

THRESH=MEAN+STANDARD DEV.

IF (THRESH≦30), THRESH=20;
IF (THRESH>50 && THRESH <100), THRESH=-THRESH+10
IF (THRESH>100 && THRESH<120), TRESH=-THRESH+20
IF (THRESH>120) THRESH=160.

Search for masses in different intensity ranges starting with the initial threshold value calculated above. This process is described below and it is repeated by increasing the threshold value by 10 until one of the following conditions is encountered:

(1) Number of masses identified exceeds five;
(2) Number of iterations exceeds three;
(3) Threshold limit is reached. This is calculated by adding the mean and four times the standard deviation.

Segment or, in other words, linarize the enhanced image starting with initial threshold value. Scan the segmented image pixel by pixel, row by row to locate each blob (concentrated density). This analysis of the image using a threshold on a pixel-by-pixel basis creates a representation of a binary image wherein the blobs or masses are represented by white areas and the background noise is represented by black areas. Calculate the height, maximum width, average width and area of each blob and apply the following conditions to either accept or reject the blob for further analysis. That is, blobs which fulfill the criteria stated below are identified as "suspicious" and may be cancerous.

AVG WIDTH≧4 and
HEIGHT≧8 AND HEIGHT≦70 and
MAX WIDTH≧6 AND MAX WIDTH≦55 AND
HEIGHT<3.3×MAX WDTH and
MAX WIDTH<2.5×HEIGHT and
AVG WIDTH<0.9×MAX WIDTH and
AREA>100

Apply the mean intensity check to the original digital image to establish that the blob located by the analysis described previously is really prominant in its immediate neighborhood as shown by Drawing 1.1 below.

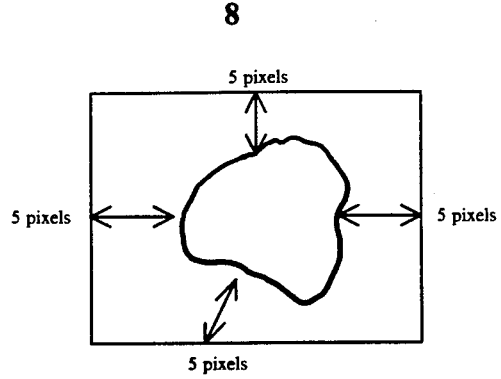

Drawing 1.1 showing blob surrounded by a rectangular area considered to be its immediate neighborhood.

For this check, calculate the mean intensity values, MEAN1 for the actual blob area and MEAN 2 for the area increased by five rows and five columns on the outermost edges of the blob. The condition for satisfying this check is given below:

MEAN1−MEAN2>DIFF (empirical value)

The empirical values for different ranges of areas are as follows:

| | | |
|---|---|---|
| AREA ≧ 900 pixels$^2$ | | DIFF ≧ 2 |
| AREA < 900 and AREA > 600 | | DIFF ≧ 5 |
| AREA ≦ 600 and AREA > 450 | | DIFF ≧ 6 |
| AREA < 450 and AREA ≧ 200 | | DIFF ≧ 9 |
| AREA < 200 and AREA ≧ 100 | | DIFF ≧ 10 |
| AREA < 100 | | DIFF ≧ 12 |
| AREA <= 300 | and AREA ≧ 80 and MEAN1 > 80 | and MEAN1 ≦ 125 and DIFF ≧ 8 |
| AREA < 300 | and AREA > 75 and MEAN1 > 70 | and MEAN1 ≦ 80 and DIFF ≧ 3 |
| AREA < 300 | and AREA > 75 and DIFF ≧ 2 | and MEAN 1 ≧ 50 |
| AREA < 300 | and AREA ≧ 200 and MEAN1 > 50 | and MEAN 1 < 60 AND DIFF ≧ 1 |
| AREA < 350 | and AREA > 80 and MEAN1 > 20 | and mean1 < 50 AND DIFF≧ 2 |

Proceed further if the blob passes this check.

Apply the shape check by calculating the following values for each blob.

$$FACTOR = \frac{(PERIMETER)^2}{AREA}$$

MAJOR AXIS =

$$1/2(MX_2 + MY_2) + 1/2 \sqrt{(MY_2 - MY_2)^2 - 4MXY}$$

MINOR AXIS =

$$1/2(MX_2 + MY^2) - 1/2 \sqrt{(MY_2 - MX_2)^2 - 4MXY}$$

... 1.0-2)

WHERE:

$$MX_2 = \left(\frac{\Sigma\Sigma P(i,j)*j^2}{M_o}\right) - MY_1^2$$

$$MY_2 = \left(\frac{\Sigma\Sigma P(i,j)*i^2}{M_o}\right) - MX_1^2$$

-continued $$MXY = \left(\frac{\Sigma\Sigma P(i,j)*i*j}{M_o}\right) - MX_1 * MY_1$$

where:

$$MX_1 = \frac{\sum_{J=0}^{255}\sum_{i=0}^{255} P(i,j)*i}{M_o}$$

$$MY_1 = \frac{\Sigma\Sigma P(i,j)*j}{M_o}$$

where:

$$MX_o = MY_o = M_o = \sum_{J=0}^{255}\sum_{i=0}^{255} P(i,j)$$

$$\text{Eccentricity} = \frac{\text{MINOR AXIS}}{\text{MAJOR AXIS}}$$

Compare FACTOR and Eccentricity values against the empirically determined values given below.

```
AREA ≧75.0&<120 & FACTOR<12&>10 pixels2
AREA ≧75.0&<90  & FACTOR<16.5&>10&Ecc>0.40&<0.65
AREA ≧90.0&<120 & FACTOR<17.0&>12&Ecc>0.36&<0.65
AREA ≧120.0&<200 & FACTOR<16.0&>11.0
AREA ≧120.0&<150 & FACTOR<22.0&>10.0&Ecc>0.35&<0.70
AREA ≧150.0&<200 & FACTOR<25.0&>10.0&Ecc>0.34&<0.70
AREA ≧200.0&<350 & FACTOR<23.0&>11.0
AREA ≧200&<280 & FACTOR<30.0&>13.0&Ecc>0.38&<0.8
AREA ≧280&<350 & FACTOR<33.0&>13.0&Ecc>0.48<0.6
AREA ≧350&<600 & FACTOR <30.0&>11.0
AREA ≧350&<425 & FACTOR <35.0&>14.0&Ecc>0.41&<0.65
AREA ≧425&<500 & FACTOR <36.0&>16.0&Ecc>0.42&<0.65
AREA ≧500&<600 & FACTOR <36.0&>16.0&Ecc>0.42&<0.65
AREA ≧600&<700 & FACTOR <45.0&>15.0&Ecc>0.33&<0.60
AREA ≧700&<850 & FACTOR <47&>15.0&Ecc>0.33&<0.6
AREA ≧850&<2500 & FACTOR <40&>11.0
AREA ≧850&<900 & FACTOR <60&>10.0&Ecc>0.33&<0.65
AREA ≧900&<1000 & FACTOR <65&>10.0&Ecc>0.33&<0.65
AREA ≧1000&<1100 & FACTOR <78&>10.0&Ecc>0.35&<0.80
AREA ≧1100&<1200 & FACTOR <79&>10.0&Ecc>0.4&<0.8
AREA ≧1200&<1400 & FACTOR <75&>10.0&Ecc>0.4&<0.8
AREA ≧1400&<1500 & FACTOR <30&>10.0&Ecc>0.4&<0.89
AREA ≧1500&<1800 & FACTOR <35&>10.0&Ecc>0.4&<0.92
AREA ≧1800&<3000 & FACTOR <40&>10.0&Ecc>0.4&<0.95
```

If the blob passes any one of these conditions, it is classified as potentially malignant and the system proceeds to draw a rectangle to enclose the blob.

DETECTION OF CALCIFICATIONS

Apply the filter described below to the original image to produce an image that highlights calcifications. This filter can be considered a spatial domain edge detection filter.

METHOD

Use a square (5×5) subimage area centered at (x,y), as shown in Drawing 2.0. Move the center of the subimage from pixel to pixel, starting from the top left hand corner, giving the center pixel a weighted sum, which is calculated by multiplying each of the pixel values contained within this area by the corresponding mask coefficient, calculated as follows:

$$T[f(x,y)) = -1*f(x-2,y-2) + -1*f(x-2,y-1)-1*(x-2,y)$$
$$-1*(x-2,y+1)-1*(x-2,y+2)-1*(x-1,y-2)$$
$$-2*(x-1,y-1)-2*(x-1,y)-2(x-1,y+1)$$
$$-1*(x-1,y-2)-1*(x,y-2)-2(x,y-1)$$
$$+32*(x,y)-2(x,y+1)-1(x,y+2)$$
$$-1*(x+1,y-2)-2(x+1,y-1)-2(x+1,y)$$
$$-2(x+1,y+1)-1(x+1,y+2)-1(x+2,y-2)$$
$$-1(x+2,y-1)-1(x+2,y)-1(x+2,y+1)$$
$$-1(x+2,y+2)\ldots(2.0-1)$$

| −1 (x−2,y+2) | −1 (x−2,y+1) | −1 (x−2,y) | −1 (x−2,y+1) | −1 (x−2,y+2) |
|---|---|---|---|---|
| −1 (x−1,y+x) | −2 (x−1,y+1) | −2 (x−1,y) | −2 (x−1,y+1) | −1 (x−1,y+2) |
| −1 (x,y−2) | −2 (x,y−1) | 32 (x,y) | −2 (x,y+1) | −1 (x,y+2) |
| −1 (x+1,y−2) | −2 (x+1,y−1) | −2 (x+1,y) | −2 (x+1,y+1) | −1 (x+1,y+2) |
| −1 (x+1,y=2) | −1 (x+2,y−1) | −1 (x+2,y) | −1 (x+2,y+1) | −1 (x+2,y+2) |

Drawing 2.0

Partition the image into three areas as shown below, to select areas of uniform intensity.

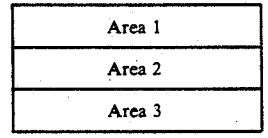

For each of these three areas, perform the following operations.

Calculate a threshold intensity value using the mean and standard deviation of intensities derived from the histogram data. Each of these threshold values should be varied slightly for each area as shown below:

For AREA 1: THRESH=MEAN=3.0 * STANDARD DEV.

For AREA 2: THRESH=MEAN+3.5 * STANDARD DEV.

For AREA 3: THRESH−MEAN+1.5 * STANDARD DEV.

Segment or, in other words, binarize the enhanced image using the initial threshold values calculated above. Count the number of blobs or points yielded by the segmentation process. Experience has shown that about 25-35 points are sufficient to identify the smallest size calcifications. Vary the threshold value until the segmentation produces a sufficient number of blobs or points. These are usually the brightest points in their immediate neighborhoods. Some of these points may not be calcifications but a few extraneous densities or film artifacts. The program uses the criteria set forth below to exclude density/artifacts and to identify calcifications. This analysis using segmented thresholding results in a representation of a binary image having the calcifications represented in white and the background noise represented in black.

Scan the segmented image with points pixel by pixel for to identify suspicious calcifications each row. If a pixel intensity of 255 is encountered, open a Window of size 24×24 pixels around that pixel. Count the number of points in window and if this number >2 and <15, this window area is to be checked for calcifications as per subsequent steps.

The suspicious calcifications are further processed to determine which, if any, are potentially malignant. If the suspiciousness condition is met, segment the enhanced image in this window only, using a slightly smaller value than that used for obtaining the maximum (20-25) number of points. (THRESH=-

THRESH−0.10×STD). Each of the blobs produced now by the segmentation process should be tested for size and shape to be able to exclude points which are too linear, or too round or too large in size. This shape check is done by finding the major and minor axis of each blob in the manner discussed above under "Detection of Masses"(Refer to 1.0-2) Apply the following conditions to satisfy the shape check:

MAJOR AXIS > 3.0 & < 12.0 and
MINOR AXIS > 2.7 & < 8.5
ECCENTRICITY < 0.99 & > 0.55

Experience with a large number of cases with different types of calcifications has shown that at least one of the calcifications in a cluster of three or more should have a major axis greater than 3.0 pixel.

Each cluster area (window) is further subjected to two more tests to exclude the extraneous densities.

Mean Value Test: The mean of intensities (MEAN1) of the cluster area is compared with the mean of intensities (MEAN2) for an extended area of three additional rows or columns outside of the window area. The condition for satisfying this check is given below:

MEAN1−MEAN 2 > DIFF (empirical value)

The empirical values for different ranges of threshold intensities are given below. These threshold intensities are calculated by obtaining the highest intensity value from the histogram data.

| | |
|---|---|
| THRESH < 50 | DIFF = 0.75 |
| THRESH > 50 & < =65 | DIFF = 1.0 |
| THRESH > 65 & < =75 | DIFF = 1.4 |
| THRESH > 75 & < =95 | DIFF = 1.8 |
| THRESH > 95 & < =105 | DIFF = 2.4 |
| THRESH > 105 & < =110 | DIFF = 2.7 |
| THRESH > 110 & < =120 | DIFF = 3.0 |
| THRESH > 120 & < =130 | DIFF = 4.0 |
| THRESH > 130 & < =150 | DIFF = 4.0 |
| THRESH > 150 & < =170 | DIFF = 4.5 |
| THRESH > 170 & < =180 | DIFF = 5.0 |

For cluster areas that are less than 100 pixel$^2$ in their size, this mean value test is not applied.

Highest Intensity Percentage Test: If the cluster area passes the above test, it is subjected to the highest intensity percentage test. Calcifications are generally high intensity points and therefore the percentage of the highest intensity points in an area with calcifications should be low as compared to non calcification areas. This percentage is calculated as follows:

$$\text{Percentage of highest intensity} = \frac{\text{highest intensity}}{\text{total area}}$$

where the highest intensity is found from the histogram data.

Test condition: Percentage < DPC (empirical value)

The empirical values for different ranges of threshold intensities are given below. These threshold values are calculated by obtaining the highest intensity value from the histogram data.

| | |
|---|---|
| THRESH < = 50 | DPC = 1.8 |
| THRESH > 50 & < =80 | DPC = 1.6 |
| THRESH > 80 & < =100 | DPC = 0.75 |
| THRESH > 100 & < =120 | DPC = 0.43 |
| THRESH > 120 & < =140 | DPC = 0.5 |
| THRESH > 140 & < =150 | DPC = 0.75 |
| THRESH > 150 & < =200 | DPC = 1.00 |

Proceed to draw a rectangle to enclose the cluster area that has passed all the above tests.

Although the invention has been described in connection with a preferred embodiment thereof, it will be appreciated by those skilled in the art that various changes and modifications can be made without departing from its spirit. The coverage afforded applicant is only to be determined by the claims and their equivalents.

What is claimed is:

1. In a method for assisting the investigation of a human breast for malignancies, the steps of:
   (a) converting intuitive criteria used to investigate a human breast for malignancies to specific numerical criteria;
   (b) programming a computer with said criteria;
   (c) acquiring information in said programmed computer defining a human breast;
   (d) using said computer to apply said specific numerical criteria defined by said program to said information to identify regions of said breast to be investigated, said information defining a calcification, and said step of using said computer includes applying criteria programmed into the same identifying regions having a predetermined number, size, and shape of calcifications.

2. The method of claim 1 wherein said preselected criteria that are applied, segregate regions of said breast having clusters of at least two calcifications within about one square centimeter from other portions of said breast.

3. Apparatus for assisting investigation of an object for a preselected condition, comprising:
   (a) optoelectronic means for acquiring information from an image of said object;
   (b) a table for positioning an image of said object in the field of view of said optoelectronic means;
   (c) a computer operably connected to said optoelectronic means for acquiring said information from said means and for identifying a region of said object to be investigated, said computer also being adapted to provide a reconstruction of the image viewed by said camera; and
   (d) means for outputting information defining said region.

4. In a method for assisting the investigation of a human breast for malignancies, the steps of:
   (a) acquiring information from a mammogram defining said human breast with optoelectronic means, including the step of generating a digital representation of said mammogram;
   (b) analyzing said information by applying preselected criteria to said information to identify regions of said breast defined by said information having either or both a mass and a calcification, said step of analyzing including detecting digital information in said representation defining masses in said human breast, and detecting digital information in said representation defining calcifications in said breast, and
   (c) said step of detecting digital information defining masses including applying a spatial domain sharpening filter to said digital representation including the step of defining a subimage by selecting non-adjacent rows of pixels from said digital representation as row elements of said image and selecting non-adjacent columns of pixels from said digital representation as column elements of said subimage.

5. In a method for assisting the investigation of a human breast for malignancies, the steps of:
(a) acquiring information from a mammogram defining said human breast with optoelectronic means, including the step of generating a digital representation of said mammogram;
(b) analyzing said information by applying preselected criteria to said information to identify regions of said breast defined by said information having either or both a mass and a calcification, said step of analyzing including detecting digital information in said representation defining masses in said human breast; and
(c) detecting digital information in said representation defining calcifications in said breast, including the step of applying a spatial domain edge detection filter to said digital image.

6. The method of claim 5 wherein said step of applying said spatial domain edge detection filter includes the steps of:
defining a subimage of said digital image which is centered upon a pixel;
calculating a weighted value including the steps of weighting each pixel in said subimage by multiplying each pixel intensity by a fixed mask coefficient, where each fixed mask coefficient is defined along concentric patterns centered upon said center pixel and each pattern has a different fixed coefficient value, and summing all of said weighted pixel values;
assigning said weighted value of said subimage to said center pixel;
moving said subimage such that a different pixel is centered; and
repeating said applying and moving steps until all of said pixels of said digital image have been assigned said weighted value.

7. The method of claim 6 wherein said step of weighting each pixel within the subimage includes weighting the center pixel by multiplying the pixel value by the number 32, weighting all pixels adjacent to the center pixel by multiplying the pixel value by the number −2, and weighting the pixels adjacent to the −2 weighted pixels by multiplying the pixel value of the same by the number −1.

8. The method of claim 5 further including the steps of:
partitioning said filtered digital representation into two or more segments of substantially uniform intensity;
calculating a mean and standard deviation of said intensity in each of said segments;
determining a threshold in each of said segments based upon said calculated means and standard deviation;
segmenting said filtered digital representation by applying said threshold to create a second binary representation.

9. The method of claim 8 further including the step of applying a second preselected criteria to said second binary image by:
determining a cluster density for said calcifications in said second binary image;
comparing determined cluster density to a preselected cluster density criteria;
acquiring information about calcifications which fulfill said second preselected criteria.

10. The method of claim 9 wherein said second preselected cluster density criteria is fulfilled by clusters of two or more calcifications located in a specified area of said digital representation.

11. In a method for assisting the investigation of a human breast for malignancies, the steps of:
(a) acquiring information from a mammogram defining said human breast with optoelectronic means, including the step of generating a digital representation of said mammogram;
(b) analyzing said information by applying preselected criteria to said information to identify regions of said breast defined by said information having either or both a mass and a calcification, said step of analyzing including detecting digital information in said representation defining masses in said human breast, and detecting digital information in said representation defining calcifications in said breast; further including the steps of:
applying a spatial domain sharpening filter to said digital representation;
partitioning said filtered digital representation into two or more segments of substantially uniform intensity;
calculating a means and standard deviation of said intensity in each of said segments;
determining a threshold in each of said segments based upon said calculated means and standard deviation; and
segmenting said filtered digital representation by applying said threshold to create a first binary representation.

12. The method of claim 11 including the step of applying a first preselected criteria to said first binary representation by:
determining an average and maximum width of said masses in said first binary image;
comparing said mass average and maximum width to a preselected width criteria;
determining the height of said masses in said first binary image;
comparing said height of said masses to a preselected height criteria;
determining the area of said masses in said first binary image;
comparing said area of said masses to a preselected area criteria; and
acquiring information about masses which fulfill said first preselected criteria.

13. In a method for assisting the investigation of a human breast for malignancies, the steps of:
(a) acquiring information with optoelectronic means from a mammogram defining said human breast; and thereafter
(b) analyzing said information by applying preselected criteria to said information to identify regions of said breast defined by said information having either or both a mass and a calcification including the steps of:
generating a substantially rectangular window in said digital representation surrounding each of said masses;
measuring the height and width of said substantially rectangular windows;

determining the area of each of said masses;

calculating a perimeter of each of said masses;

calculating a factor having the steps of squaring said perimeter and dividing said squared perimeter by said area of each of said masses;

determining the length of a minor axis and a major axis of each of said masses;

calculating a ratio by dividing said minor axis length by said major axis length for each of said masses;

calculating a first mean intensity of all pixels within said substantially rectangular window;

incrementing the area of said substantially rectangular window by a fixed amount;

calculating a second means intensity of all pixels within said incremented substantially rectangular window;

determining a mean intensity difference by subtracting said first mean from said second mean;

comparing said window height and width and said mass factor, ratio, means intensity difference to a third preselected criteria; and identifying said masses to be investigated which fulfill said third preselected criteria.

14. In a method for assisting the investigation of a human breast for malignancies, the steps of:
  (a) acquiring information from a mammogram defining said human breast with optoelectronic means from a mammogram defining said human breast; and thereafter
  (b) analyzing said information by applying preselected criteria to said information to identity regions of said breast defined by said information having either or both a mass and a calcification, including the steps of:
    determining clusters of said calcifications;
    generating a substantially rectangular window surrounding each of said clusters of said calcifications;
    counting the number of said calcifications in each of said substantially rectangular windows;
    measuring a length of a major axis and a minor axis of each of said calcifications;
    calculating a ratio by dividing said length of said minor axis by said length of said major axis for each of said calcifications;
    calculating a density by dividing the area of said substantially rectangular window surrounding each of said clusters by said number of said calcifications within each of said substantially rectangular windows;
    calculating a first average intensity of an area within said substantially rectangular window surrounding each of said clusters;
    incrementing the area of said substantially rectangular window surrounding each of said clusters by a fixed amount;
    calculating a second average intensity within said incremented area of said substantially rectangular window surrounding each of said clusters;
    determining an average intensity difference by subtracting said first average intensity from said second average intensity;
    comparing said major axis, minor axis, ratio, average intensity difference, and density to a fourth preselected criteria; and
    identifying said clusters of said calcifications to be investigated with fulfill said preselected criteria.

15. The method of claim 13 or 14 wherein said preselected criteria is determined by empirical data and radiologist expertise.

16. In a method for assisting the investigation of a human breast, the steps of:
  (a) acquiring information from a mammogram of said breast with optoelectronic means, which information defines said breast; and thereafter
  (b) applying preselected criteria to said information to identify regions of said breast defined by said information to be investigated, said step of acquiring information including the step of:
    generating a digital representation of said mammogram, and said step of applying preselected criteria includes:
    detecting digital information in said representation defining masses in said human breast by applying a spatial domain sharpening filter to said digital representation, and
    wherein said step of applying said spatial domain sharpening filter includes the step of defining a subimage by selecting non-adjacent rows of pixels from said digital representation as row elements of said image and selecting non-adjacent columns of pixels from said digital representation as column elements of said subimage.

17. In a method for assisting the investigation of a human breast, the steps of:
  (a) acquiring information from a mammogram of said breast with optoelectronic means, which information defines said breast; and thereafter p1 (b) apply preselected criteria to said information to identify regions of said breast defined by said information to be investigated, said step of acquiring information including the step of:
    generating a digital representation of said mammogram, and said step of applying preselected criteria including the step of:
    detecting digital information in said representation defining masses in said human breast by applying a spatial domain sharpening filter to said digital representation, further including the steps of:
    partitioning said filtered digital representation into two or more segments of substantially uniform intensity;
    calculating a mean and standard deviation of said intensity in each of said segments;
    determining a threshold in each of said segments based upon said calculated mean and standard deviation; and
    segmenting said filtered digital representation by applying said threshold to create a first binary representation.

18. The method of claim 17 further including the step of applying a first preselected criteria to said first binary representation by:
  determining an average and maximum width of said masses in said first binary image;
  comparing said mass average and maximum width to a preselected width criteria;
  determining the height of said masses in said first binary image;
  comparing said height of said masses to a preselected height criteria;
  determining the area of said masses in said first binary image;
  comparing said area of said masses to a preselected area criteria; and acquiring information about masses which fulfill said first preselected criteria.

19. In a method for assisting the investigation of a human breast, the steps of:
   (a) acquiring information from a mammogram of said breast with optoelectronic means, which information defines said breast; and thereafter
   (b) applying preselected criteria to said information to identify regions of said breast defined by said information to be investigated, said step of acquiring information including the step of:
   generating a digital representation of said mammogram; and wherein said step of applying preselected criteria to said information includes the steps of:
   generating a substantially rectangular window in said digital representation surrounding each of said masses determined in said analyzing step;
   measuring the height and width of said substantially rectangular windows;
   determining the area of each of said masses;
   calculating a perimeter of each of said masses;
   calculating a factor having the steps of squaring said perimeter and dividing said squared perimeter by said area of each of said masses;
   determining the length of a minor axis and a major axis of each of said masses;
   calculating a ratio by dividing said minor axis length by said major axis length for each of said masses;
   calculating a first mean intensity of all pixels within said substantially rectangular window;
   incrementing the area of said substantially rectangular window by a fixed amount;
   calculating a second means intensity of all pixels within said incremented substantially rectangular window;
   determining a means intensity difference by subtracting said first means from said second means;
   comparing said window height and width and said mass factor, ratio, mean intensity difference to a third preselected criteria; and
   identifying said masses to be investigated which fulfill said third preselected criteria.

20. The method of claim 19 wherein said preselected criteria is determined by empirical data and radiologist expertise.

21. In a method for assisting the investigation of a human breast for malignancies, the steps of:
   (a) acquiring information from a mammogram of said human breast with optoelectronic means, including the step of generating a digital image of said mammogram;
   (b) applying preselected criteria to said information to identify regions of said breast defined by said information to be investigated including the step of detecting information in said image defining calcifications in said human breast and applying a spatial domain edge detection filter to said digital image, and:
   said step of applying said spatial edge detection filter includes the steps of:
   defining a subimage of said digital image which is centered upon a pixel;
   calculating a weighted sum value including the steps of weighting each pixel in said subimage by multiplying each pixel intensity by a fixed mask coefficient, where each fixed mask coefficient is defined along concentric patterns centered upon said center pixel and each pattern has a different fixed coefficient value, and summing all of said weighted pixel values;
   assigning said weighted sum value of said subimage to said center pixel;
   moving said subimage such that a different pixel is centered; and
   repeating said applying and moving steps until all of said pixels of said digital image have been assigned said weighted sum value.

22. The method of claim 21 wherein said step of weighting each pixel within the subimage includes weighting the center pixel with the number 32, weighting all pixels adjacent to the center pixel with the number $-2$, and weighting the pixels adjacent to the $-2$ weighted pixels with the number $-1$.

23. In a method for assisting the investigation of a human breast for malignancies, the steps of:
   (a) acquiring information from a mammogram of said human breast with optoelectronic means, including the step of generating a digital image representation of said mammogram;
   (b) applying preselected criteria to said information to identify regions of said breast defined by said information to be investigated including the step of detecting information in said image defining calcifications in said human breast and applying a spatial domain edge detection filter to said digital image representation, further including the steps of:
   partitioning said filtered digital representation into two or more segments of substantially uniform intensity;
   calculating a mean and standard deviation of said intensity in each of said segments;
   determining a threshold in each of said segments based upon said calculated mean and standard deviation; and
   segmenting said filtered digital representation by applying said threshold to create a first binary representation.

24. The method of claim 23 further including the step of applying a second preselected criteria to said first binary image by:
   determining a cluster density for said calcifications in said second binary image;
   comparing determined cluster density to a preselected cluster density criteria; and
   acquiring information about calcifications which will fulfill said selected criteria.

25. The method of claim 24 wherein said second preselected cluster density criteria is fulfilled by clusters of two or more calcifications located in a specified area of said digital representation.

26. In a method for assisting the investigation of a human breast for malignancy, the steps of:
   (a) acquiring information from a mammogram of said human breast with optoelectronic means; and thereafter
   (b) analyzing said information by applying preselected criteria to said information to identify regions of said breast having calcifications, said step including the steps of:
   determining clusters of said calcifications;
   generating a substantially rectangular window surrounding each of said clusters of said calcifications;

counting the number of said calcifications in each of said substantially rectangular windows;

measuring a length of a major axis and a minor axis of each of said calcifications;

calculating a ratio by dividing said length of said minor axis by said length of said major axis for each of said calcifications;

calculating a density by dividing the area of said substantially rectangular window surrounding each of said clusters by said number of said calcifications within each of said substantially rectangular windows;

calculating a first average intensity of an area within said substantially rectangular window surrounding each of said clusters;

incrementing the area of said substantially rectangular window surrounding each of said clusters by a fixed amount;

calculating a second average intensity within said incremented area of said substantially rectangular window surrounding each of said clusters;

determining an average intensity difference by subtracting said first average intensity from said second average intensity;

comparing said major axis, minor axis, ratio, average intensity difference, and density to a fourth preselected criteria; and identifying said clusters of said calcifications which fulfill said preselected criteria to be investigated.

27. The method of claim 26 wherein said preselected criteria is determined by empirical data and radiologist expertise.

* * * * *